United States Patent
Lichenstein et al.

(10) Patent No.: US 10,285,959 B2
(45) Date of Patent: May 14, 2019

(54) COMBINATION THERAPIES USING HDAC INHIBITORS

(71) Applicant: TopoTarget UK Limited, Abingdon, Oxfordshire (GB)

(72) Inventors: Henri Lichenstein, Branford, CT (US); Mike Jeffers, Branford, CT (US); Xiaozhang Qian, Branford, CT (US); Maxwell Sehested, Copenhagen (DK); Kamille Dumong Erichsen, Copenhagen (DK); James Ritchie, Oxfordshire (GB)

(73) Assignee: TopoTarget UK Limited (GB)

( * ) Notice: Subject to any disclaimer, the term of this patent is extended or adjusted under 35 U.S.C. 154(b) by 0 days.

(21) Appl. No.: 14/554,261

(22) Filed: Nov. 26, 2014

(65) Prior Publication Data
US 2015/0231096 A1    Aug. 20, 2015

Related U.S. Application Data

(63) Continuation of application No. 11/815,372, filed as application No. PCT/GB2006/000391 on Feb. 3, 2006, now abandoned.
(Continued)

(51) Int. Cl.
*A61K 31/18* (2006.01)
*A61K 31/24* (2006.01)
(Continued)

(52) U.S. Cl.
CPC ............ *A61K 31/18* (2013.01); *A61K 31/138* (2013.01); *A61K 31/196* (2013.01);
(Continued)

(58) Field of Classification Search
None
See application file for complete search history.

(56) References Cited

U.S. PATENT DOCUMENTS

| | | | |
|---|---|---|---|
| 4,642,316 | A | 2/1987 | Fawzi et al. |
| 6,071,923 | A | 6/2000 | Nudelman et al. |

(Continued)

FOREIGN PATENT DOCUMENTS

| | | | |
|---|---|---|---|
| EP | 0787742 A1 | 8/1997 | |
| EP | 1293205 A1 | 3/2003 | |

(Continued)

OTHER PUBLICATIONS

Merck Manual: Home Edition, titled: Combination therapy. Chabner et al. Aug. 2007. Electronic Resource: [http://merck.com/mmhe/sec15/ch182/ch182h.html}. Retrieved online on Sep. 11, 2010.*
(Continued)

*Primary Examiner* — Anna Pagonakis
(74) *Attorney, Agent, or Firm* — Lerner, David, Littenberg, Krumholz & Mentlik, LLP

(57) ABSTRACT

The present invention pertains to a method for treating cancer, such as lung cancer, multiple myeloma, lymphoma, and epithelial ovarian cancer, comprising the administration to a patient in need thereof a first amount or dose of a histone deacetylase (HDAC) inhibitor, such as PXD-101, and a second amount or dose of another chemotherapeutic agent, such as dexamethasone or 5-fluorouracil, or an epidermal growth factor receptor (EGFR) inhibitor, such as TarcevaÜ, wherein the first and second amounts or doses together comprise a therapeutically effective amount.

1 Claim, 4 Drawing Sheets

Related U.S. Application Data

(60) Provisional application No. 60/735,662, filed on Nov. 10, 2005, provisional application No. 60/649,991, filed on Feb. 3, 2005.

(51) Int. Cl.

| | |
|---|---|
| *A61K 33/24* | (2006.01) |
| *A61K 45/06* | (2006.01) |
| *A61K 31/138* | (2006.01) |
| *A61K 31/196* | (2006.01) |
| *A61K 31/198* | (2006.01) |
| *A61K 31/282* | (2006.01) |
| *A61K 31/337* | (2006.01) |
| *A61K 31/475* | (2006.01) |
| *A61K 31/513* | (2006.01) |
| *A61K 31/517* | (2006.01) |
| *A61K 31/519* | (2006.01) |
| *A61K 31/555* | (2006.01) |
| *A61K 31/573* | (2006.01) |
| *A61K 31/704* | (2006.01) |
| *A61K 31/706* | (2006.01) |
| *A61K 31/4745* | (2006.01) |
| *A61K 31/7068* | (2006.01) |
| *A61K 31/7076* | (2006.01) |

(52) U.S. Cl.
CPC ............ *A61K 31/198* (2013.01); *A61K 31/24* (2013.01); *A61K 31/282* (2013.01); *A61K 31/337* (2013.01); *A61K 31/475* (2013.01); *A61K 31/4745* (2013.01); *A61K 31/513* (2013.01); *A61K 31/517* (2013.01); *A61K 31/519* (2013.01); *A61K 31/555* (2013.01); *A61K 31/573* (2013.01); *A61K 31/704* (2013.01); *A61K 31/706* (2013.01); *A61K 31/7068* (2013.01); *A61K 31/7076* (2013.01); *A61K 33/24* (2013.01); *A61K 45/06* (2013.01); *A61K 2300/00* (2013.01)

(56) References Cited

U.S. PATENT DOCUMENTS

| | | | |
|---|---|---|---|
| 6,342,219 | B1 | 1/2002 | Thorpe et al. |
| 6,541,661 | B1 | 4/2003 | Delorme et al. |
| 6,656,905 | B1 | 12/2003 | Mori et al. |
| 6,888,027 | B2 | 5/2005 | Watkins et al. |
| 7,183,298 | B2 | 2/2007 | Watkins et al. |
| RE39,850 | E | 9/2007 | Delorme et al. |
| 7,375,137 | B2 | 5/2008 | Bacopoulos et al. |
| 7,407,988 | B2 | 8/2008 | Kalvinsh et al. |
| 7,465,731 | B2 | 12/2008 | Ishibashi et al. |
| 7,491,748 | B2 | 2/2009 | Tani et al. |
| 7,495,022 | B2 | 2/2009 | Kim et al. |
| 7,557,140 | B2 | 7/2009 | Kalvinsh et al. |
| 2003/0161830 | A1* | 8/2003 | Jackson ............... C12N 9/16 424/146.1 |
| 2003/0170319 | A1 | 9/2003 | Netke et al. |
| 2003/0235588 | A1 | 12/2003 | Richon et al. |
| 2004/0018968 | A1 | 1/2004 | Sgouros et al. |
| 2004/0072735 | A1 | 4/2004 | Richon et al. |
| 2004/0077726 | A1 | 4/2004 | Watkins et al. |
| 2004/0092598 | A1 | 5/2004 | Watkins et al. |
| 2004/0127523 | A1 | 7/2004 | Bacopoulos et al. |
| 2004/0132825 | A1 | 7/2004 | Bacopoulos et al. |
| 2004/0198830 | A1 | 10/2004 | Watkins et al. |
| 2004/0220242 | A1 | 11/2004 | Shapiro |
| 2004/0254220 | A1 | 12/2004 | Bressi et al. |
| 2005/0085515 | A1 | 4/2005 | Watkins et al. |
| 2005/0107445 | A1 | 5/2005 | Watkins et al. |
| 2005/0119305 | A1 | 6/2005 | Naka et al. |
| 2005/0124679 | A1 | 6/2005 | Kim et al. |
| 2005/0222013 | A1 | 10/2005 | Jung et al. |
| 2005/0245439 | A1 | 11/2005 | Chung |
| 2005/0288227 | A1 | 12/2005 | Marks et al. |
| 2006/0052599 | A1 | 3/2006 | Ishibashi et al. |
| 2006/0058298 | A1 | 3/2006 | Delorme et al. |
| 2006/0160897 | A1 | 7/2006 | Pelicci et al. |
| 2006/0229237 | A1 | 10/2006 | Chung et al. |
| 2006/0270016 | A1 | 11/2006 | Holm |
| 2007/0004806 | A1 | 1/2007 | Kalvinsh et al. |
| 2007/0037738 | A1 | 2/2007 | Hentsch et al. |
| 2007/0054260 | A1 | 3/2007 | Trepel et al. |
| 2007/0060614 | A1 | 3/2007 | Bacopoulos et al. |
| 2007/0110719 | A1 | 5/2007 | Holm |
| 2007/0148228 | A1 | 6/2007 | Cumming et al. |
| 2007/0232528 | A1 | 10/2007 | Franke |
| 2007/0292512 | A1 | 12/2007 | Leonard et al. |
| 2008/0004311 | A1 | 1/2008 | Hellberg |
| 2008/0045445 | A1 | 2/2008 | Chen et al. |
| 2008/0119424 | A1 | 5/2008 | Bernards et al. |
| 2008/0146623 | A1 | 6/2008 | Deziel et al. |
| 2008/0161401 | A1 | 7/2008 | Watkins et al. |
| 2008/0194690 | A1 | 8/2008 | Bastin et al. |
| 2008/0207724 | A1 | 8/2008 | Mink et al. |
| 2008/0213399 | A1 | 9/2008 | Lichenstein et al. |
| 2008/0214547 | A1 | 9/2008 | Srivastava et al. |
| 2008/0242648 | A1 | 10/2008 | Ordentlich et al. |
| 2008/0249137 | A1 | 10/2008 | Lin et al. |
| 2008/0249179 | A1 | 10/2008 | Bacopoulos et al. |
| 2008/0274120 | A1 | 11/2008 | Lichenstein et al. |
| 2008/0292616 | A1 | 11/2008 | Bates et al. |
| 2009/0012175 | A1 | 1/2009 | Bacopoulos et al. |
| 2009/0023149 | A1 | 1/2009 | Knudsen |
| 2009/0036435 | A1 | 2/2009 | Curry et al. |
| 2009/0048156 | A1 | 2/2009 | Brodie et al. |
| 2009/0060873 | A1 | 3/2009 | Sporn et al. |
| 2009/0098054 | A1 | 4/2009 | Kufe |
| 2009/0105168 | A1 | 4/2009 | Gruber et al. |
| 2009/0142337 | A1 | 6/2009 | Squires |
| 2009/0186809 | A1 | 7/2009 | Hentsch et al. |
| 2009/0232800 | A1 | 9/2009 | Holm |
| 2009/0233902 | A1 | 9/2009 | Vennemann et al. |
| 2009/0246169 | A1 | 10/2009 | Vennemann et al. |
| 2009/0246198 | A1 | 10/2009 | Dong et al. |
| 2009/0270497 | A1 | 10/2009 | Buggy |
| 2009/0286862 | A1 | 11/2009 | Narita et al. |
| 2009/0298924 | A1 | 12/2009 | Davidson et al. |
| 2009/0311175 | A1 | 12/2009 | Brose |

FOREIGN PATENT DOCUMENTS

| | | | |
|---|---|---|---|
| EP | 1426054 | A1 | 6/2004 |
| JP | 10114681 | | 5/1998 |
| WO | 02/26696 | A1 | 4/2002 |
| WO | 02/30879 | A2 | 4/2002 |
| WO | 2002090534 | | 11/2002 |
| WO | WO 2003/024442 | * | 3/2003 |
| WO | 2003066579 | | 8/2003 |
| WO | 2003075929 | | 9/2003 |
| WO | 2003082286 | | 10/2003 |
| WO | 2003087057 | | 10/2003 |
| WO | 2003092686 | | 11/2003 |
| WO | 2004009536 | A1 | 1/2004 |
| WO | 2004013130 | A1 | 2/2004 |
| WO | 2004043962 | A1 | 5/2004 |
| WO | 2004063146 | A1 | 7/2004 |
| WO | 2004063169 | A1 | 7/2004 |
| WO | 2004064 727 | A2 | 8/2004 |
| WO | 2004069803 | A2 | 8/2004 |
| WO | 2004069823 | A1 | 8/2004 |
| WO | 2004071400 | A2 | 8/2004 |
| WO | 2004072047 | A1 | 8/2004 |
| WO | WO 2004/064727 | * | 8/2004 |
| WO | 2004074451 | A2 | 9/2004 |
| WO | 2004082638 | A2 | 9/2004 |
| WO | 2004087693 | A1 | 10/2004 |
| WO | 2004092115 | A2 | 10/2004 |
| WO | 2004103358 | A2 | 12/2004 |
| WO | 2005000901 | A2 | 1/2005 |
| WO | 2005023179 | A2 | 3/2005 |

(56) References Cited

FOREIGN PATENT DOCUMENTS

| WO | WO 2005/023179 | * | 3/2005 |
|---|---|---|---|
| WO | 2005063806 A1 | | 7/2005 |
| WO | 20060 12688 A1 | | 2/2006 |
| WO | 2006064121 A2 | | 6/2006 |
| WO | 2006082428 A2 | | 8/2006 |
| WO | 2006120456 A1 | | 11/2006 |
| WO | 2007049262 A1 | | 5/2007 |
| WO | 2007110623 A2 | | 10/2007 |
| WO | 2008090534 A1 | | 7/2008 |

OTHER PUBLICATIONS

Perez-Soler et al. Determinants of tumor response and survival with erlotinib in patients with non-small cell lung cancer. J. Clin. Oncol. 22: 3238-3247. Aug. 15, 2004.*
Bonomi. Erlotinib: a new therapeutic approach for non-small cell lung cancer. Expert Opin. Investig. Drugs, 2003, 12(8).*
Plumb et al. Pharmacodynamic response and inhibition of growth of human tumor xenografts by the novel histone deacetylase inhibitor PXD101. vol. 2, 721-728, Aug. 2003.*
Witta et al. Overcoming resistance to EGFR inhibitors in NSCLC cell lines by sequential treatment with histone deacetylase inhibitors. Journal of Clinical Oncology, 2005 ASCO Annual Meeting Proceedings, vol. 23, No. 16S (Jun. 1 Supplement), 2005: 7083.*
Siegel-Lakhai et al. Current knowledge and future directions of the selective epidermal growth receptor inhibitors erlotinib (tarceva) and gefitinib. Sep. 2005; 10: 579-589.*
Yoshida, M. et al. Trichostatin and leptomycin: inhibition of histone deacetylation and signal-dependent nuclear export. Ann. Ny. Y. Acad. Sci., 1999; 886: 23-36.
Yoshida, M. et al. "Reversible Arrest of Proliferation of rat 3Y1 Fibroblasts in Both G1 and G2 Phases by Trichostatin A." Exp. Cell. Res., 1988; 177(1): 122-131.
Yoshida, M. et al. "Potent and Specific Inhibition of Mammalian Histone Deacetylase Both in Vivo and in Vitro by Trichostatin A." J. Bioi. Chern, 1990; 265(28):17174-17179.
Yoshida, M. et al. "Structural Specificity for Biological Activity of Trichostatin A, a Specific Inhibitor of Mammalian Cell Cycle with Potent Differentiation-Inducing Activity in Friend Leukemia Cells." J. Antibiot. (Tokyo), 1990; 43(9): 1101-1106.
Zenger, M. et al. "Chapter 27: Structure-Activity Relationship and Drug Design." Remington's Pharmaceutical Sciences, 16th Ed. (1980): pp. 420-425.
Bouchain, G. et al., "Development of potential antitumor agents. Synthesis and biological evaluation of a new set of sulfonamide derivatives as histone deacetylase inhibitors," J. Med. Chern., Feb. 27, 2003, vol. 46, No. 5, pp. 820-830.
Dorwald et al., "Side reactions in organic synthesis: A guide to successful synthesis design," Weinheim: WILEY-VCH Verlag GmbH & Co. KgaA, 2005, Preface.
Emiliani, S. et al., "Characterization of a human RPD3 ortholog, HDAC3," Proc. Natl. Acad. Sci. U. S. A., Mar. 17, 1998, vol. 95, No. 6, pp. 2795-2800.
Finnin, M.S. et al., "Structures of a histone deacetylase homologue bound to the TSA and SAHA inhibitors," Nature, Sep. 9, 1999, vol. 401, No. 67 49, pp. 188-193.
Grozinger, C. M. et al., "Three proteins define a class of human histone deacetylases related to yeast Hda1p," Proc. Natl. Acad. Sci. U.S. A., Apr. 27, 1999, vol. 96, No. 9, pp. 4868-4873.
Kim, M.S. et al., "Histone deacetylases induce angiogenesis by negative regulation of tumor suppressor genes," Nat. Med. Apr. 2001, vol. 7, No. 4, pp. 437-443.
Andrews et al. "Anti-malarial Effect of Histone Deacetylation Inhibitors and Mammalian Tumour Cytodifferentiating Agents." Int. J. Parasitol., 2000; 30(6): 761-768.
Bernhard, D. et al. "Apoptosis Induced by the Histone Deacetylase Inhibitor Sodium Butyrate in Human Leukemic Lymphoblasts_" FASEB J., 1999; 13(14): 1991-2001.

Bernstein, B. E. et al., Genomewide studies of histone deacetylase function in yeast. Proc Natl Acad Sci USA. Dec. 5, 2000, vol. 97, No. 25, pp. 13708-13713. Erratum in: Proc Natl Acad Sci USA Apr. 24, 2001, vol. 98, No. 9, pp. 5368.
Brehm, A. et al. "Retinoblastoma Protein Recruits Histone Deacetylase to Repress Transcription." Nature, 1998; 391(6667): 597-601.
Chang et al. "Activation of the BRLF1 Promoter and Lytic Cycle of Epstein-Barr Virus by Histone Acetylation." Nucleic Acids Res., 2000; 28(20):3918-3925.
Dangond et al. "Differential Display Cloning of a Novel Human Histone Deacetylase (HDAC3) eDNA from PHA-Activated Immune Cells." Biochem. Biophys. Res. Commun., 1998; 242(3): 648-652.
David, G. et aL "Histone Deacetylase Associated with mSin3A Mediates Repression by the Acute Promyelocytic Leukemia-associated PLZF Protein." Oncogene, 19 98; 16(1 9): 2549-2556.
Davie, J.R "Covalent Modifications of Histones: Expression from Chromatin Templates." Curr. Opin. Genet Dev., 1998; 8(2): 173-178.
Aravantinos G. et al., "Phase II study of docetaxel-vinorelbine in platinum-resistant, paclitaxel-pretreated ovarian cancer." Ann. Oncol. Jul. 2003, 14 (7); 1094-1099.
Chou, T. C. "Theoretical basis, experimentaldesign, and computerized simulation of synergism and antagonism in drug combination studies." Pharmacol. Rev. Sep. 2006; 58(3): 621-81.
Hamilton, T. C. et al., "Characterization of a human ovarian carcinoma cell line (NIH:OVCAR-3) with androgen and estrogen receptors." Cancer Res. Nov. 1983; 43(11):5379-89.
Kuzuya, K. et al., "Optimal doses of paclitaxel and carboplatin combination chemotherapy for ovarian cancer: a phase I modified continual reassessment method study." Int. J. Clin. Oncol. Dec. 2001; 6(6):271-8.
Paris, M. et al., "Histone deacetylase inhibitors: from bench to clinic." J Med Chem. Mar. 27, 2008; 51{6):1505-29. Epub Feb. 5, 2008.
Thigpen, J. T. et al., Second-line chemotherapy for recurrent carcinoma of the ovary. Cancer. Feb. 15, 1993; 71(4 Suppl): 1559-64.
"Guidance for Industry: S1C{R2) Dose selection for carcinogenicity studies," U.S. Department of Health and Human Services. Food and Drug Administration, Center for Drug Evaluation and Research (COER). Center for Biologics Evaluation and Research (CBER), Sep. 2008.
Berenbaum et al. What is synergy? Pharmacological Reviews, 1989.
Adler, J.T. et al., "Inhibition of Growth in Medullary Thyroid Cancer Cells with Histone Deacetylase Inhibitors andLithium Chloride", Journal of SurgicalResearch, (2010), vol. 159, pp. 640-644.
Arnold.N.B. et al., "The Histone Deacetylase Inhibitor Suberoylanilide Hydroxamci Acid Induces Growth Inhibition and Enhances Gemcitabine-Induced Cell Death in Pancreatic Cancer", Clin. Cancer Res.. (2007).vol. 13, pp. 18-26.
Banwell, C.M. et al., "Targeting 1alpha.25-dihydroxyvitamin D3 Antiproliferative Insensitivity in Breast Cancer Cells by Co-Treatment with Histone Deacetylation Inhibitors", Journal of Steroid Biochemistry & Molecular Biology, (2004). vol. 89-90, pp. 245-249.
Baradari, V. et al., "Histone Deacetylase Inhibitor MS-275 Alone or Combined with Bortezomib or Sorafenib ExhibitsStrong Antiproliferative Action in Human Cholangiocarcinoma Cells".World Journalof Gastroenterology, (Sep. 7, 2007), vol. 13, No. 33, pp. 4458-4466.
Bolden, J. E. et al., Anticancer activities of histone deacetylase inhibitors,o Nat. Rev. Drug Discov., Sep. 2006, vol. 5, No. 9, pp. 769-784.
Bookman, M. A. et al., "Extending the platinum-free interval in recurrent ovarian cancer: the role of topotecan in second-line chemotherapy," Oncologist, 1999, vol. 4, No. 2, pp. 87-94.
Dalgard, C.L. et al., "Evaluation of the In vitro and In vivo Antitumor Activity of Histone Deacetylase Inhibitors for the Therapy of Retinoblastoma", Clinical Cancer Research, (2008), vol. 14, pp. 3113-3123.
De Los Santos, M. et al., "Anti-estrogenic Actions of Histone Deacetylase Inhibitors in MCF-7 Breast Cancer Cells", Endocrine-Related Cancer, (2007), vol. 14, pp. 1021-1028.

(56) References Cited

OTHER PUBLICATIONS

De Ruijter, A.J.M. et al., "Antagonistic Effects of Sequential Administration of BL 1521, a Histone Deacetylase Inhibitor, and Gemcitabine to Neuroblastoma Cells", Cancer Letters, (2006), vol. 233, pp. 240-246.
Entin-Meer, M. et al., "An-113, a Novel Prodrug of 4-Phenylbutyrate with Increased Anti-neoplastic Activity in Glioma Cell Lines", (2007), vol. 253, pp. 205-214.
Hurtubise, A. et al., "Effect of Histone Deacetylase Inhibitor LAQ824 on Antineoplastic Action of 5-Aza-2'-deoxycytidine (Decitabine) on Human Breast Carcinoma Cells", Cancer Chemother. Pharmacal., (2006), vol. 58, pp. 618-625.
Jang, E.-R. et al., "Different Effect of Protein Kinase B/Akt and Extrcellular Signal-Regulated Kinase Inhibition on 12 Trichostatin A-Induced Apoptosis in Epithelial Ovarian Carcinoma Cell Lines", Mol. Cell Biochem., (2011 ), vol. 353, pp. 1-11.
Kano, Y. et al., "Cytotoxic Effects of Histone Deacetylase Inhibitor FK228 (Depsipeptide, formerly named FR901228) in Combination with Conventional Anti-Leukemia/Lymphoma Agents Against Human Leukemia/Lymphoma Cell Lines", Invest. New Drugs, (2006), vol. 25, pp. 31-40.
Khan, S.B. et al., "Analysis of Histone Deacetylase Inhibitor, Depsipeptide (FR901228), Effect on Multiple Myeloma", British Journal of Haematology, (2004), vol. 125, pp. 156-161.
Kim, J.C. et al., "In Vitro Evaluation of Histone Deacetylase Inhibitors as Combination Agents for Colorectal Cancer", Anticancer Research, (2009), vol. 29, pp. 3027-3034.
Lai, J.-P. et al., "Additive Effect of Apicidin and Doxorubicin in Sulfatase 1 Expressing Hepatocellular Carcinoma In Vitro and In vivo", Journal of Hepatology, vol. 50, pp. 1112-1121.
Li, P. et al., "Coordination of PAD4 and HDAC2 in the Regulation of p53-Target Gene Expression", (2010), vol. 29, pp. 3153-3162.
Peng, C.-Y. et al., "Growth-Inhibiting Effects of Arsenic Trioxide Plus Epigenetic Therapeutic Agents on Leukemia Cell Lines", Leukemia & Lymphoma, (Feb. 2010), vol. 51, No. 2, pp. 297-303.
Rovida, E. et al., "The c-Jun-N-terminai-Kinase Inhibitor SP600125 Enhances the Butyrate Derivative D1-Induced Apoptosis Via Caspase 8 Activation in Kasumi 1 t(8;21) Acute Myeloid Leukaemia Cells", British Journal of Haematology, (2006), vol. 135, pp. 653-659.
Sonnemann, J. et al., "Comparative Evaluation of the Treatment Efficacy of Suberoylanilide Hydroxamic Acid (SAHA) and Paclitaxel in Ovarian Cancer Cell Lines and Primary Ovarian Cancer Cells from Patients", BMC Cancer, (2006), vol. 6, pp. 183.
Taddei, A. et al., "The Effects of Histone Deacetylase Inhibitors on Heterochromatin: Implications for Anticancer Therapy", EMBO Reports, (2005), vol. 6, No. 6, pp. 520-524.
Touma, S.E. et al., "Retinoic Acid and the Histone Deacetylase Inhibitor Trichostatin A Inhibit the Proliferation of Human Renal Cell Carcinoma in a Xenograft Tumor Model", Clinical Cancer Research, (2005), vol. 11, pp. 3558-3566.
Wedel, S. et al., "Inhibitory Effects of the HDAC Inhibitor Valproic Acid on Prostrate Cancer Growth are Enhanced by Simultaneous Application of mTOR Inhibitor RAD001", Life Sciences, (2011 ), val. 88, pp. 418-424.
Ozols. Recurrent ovarian cancer: Evidence-based treatment. Journal of Clinical Oncology, vol. 20, No. 5, Mar. 1, 2002, pp. 1161-1163.
Havrilesky et al. Weekly low-dose carboplatin and paclitaxel in the treatment of recurrent ovarian and peritoneal cancer. Gynecologic Cancer, 88, 51-57, 2003.
Vippagunta, et al. Advanced Drug Delivery Reviews, 48, 2001, p. 18.
Jordan, V. C. Nature Reviews: Drug Discovery, 2, 2003, pp. 205-213.
Vasey et al. Phase III randomized trial of docetaxel-carboplatin versus paclitaxel-carboplatin as first-line chemotherapy for ovarian carcinoma. J. Natl. Cancer Inst. 2004; 96: 1682-91.
Nejit et al. Paclitaxel/carboplatin for the initial treatment of advanced ovarian cancer. Seminars in Oncology, vol. 26, Suppl. 2 Feb. 1999, pp. 78-83.

Plumb et al. Pharmacodynamic response and inhibiiton of growht of human tumor xenografts by the novel histone deacetylase inhibitor, PXD-1 01. Molecular Cancer Therapeutics, vol. 2, 721-728, Aug. 2003.
Yang et al. Knockdown of Rab25 expression by RNAi inhibits growth of human epithelial ovarian cancer cells in vitro and in vivo. Pathology, Dec. 2006, 38(6), pp. 561-567.
"Topotarget aims for top of class," Bioventure View (2004) 19(13):11.
"TopoTarget and CuraGen advance HDAC inhibitor PXD101 into Phase II clinical trials," Press Release dated Feb. 1, 2005 and retrieved from the Internet 2006 (URL: http://www.topotarget.com/Multimedia/19-_pressrelease_01 022005.pdf).
American Cancer Society Inc., "Cancer Facts and Figures 2003," (2003) 1-52.
Bast, R.C. et al., "Chapter 321: Ovarian Cancer," in Harrison's Principles of Internal Medicine, 13th edition, Isselbacher et al., eds., McGraw-Hill, New York, 1853-1858.
Berge et al., "Pharmaceutical salts," J. Pharm. Sci. (1977) 66:1-19.
Jensen, P.B. et al., "Differential cytotoxicity of 19 anticancer agents in wild type and etoposide resistant small cell lung cancer cell lines," Br. J. Cancer (1993) 67:311-320.
Knies-Bam Forth, U., "Fight against cancer taking centre stage in Boston," Drug Discovery Today, Elsevier Science Limited, GB (2004) 9(23):998-999.
Pauer, L.R. et al., "Phase I study of oral CI-994 in combination with Carboplatin and Paclitaxel in the treatment of patients with advanced solid tumors," Cancer Investigation (2004) 22(6):886-896.
Plumb, J.A. et al., "Epigenetic approaches to cancer therapy," Biochem. Soc. Transactions (2004) 32(6):1095-1097.
Ritchie, J. et al., "The histone deacetylase inhibitor PXC101 synergises with established chemotherapeutics to inhibit tumour cell proliferation and upregulate apoptosis in vitro," Clinical Cancer REs. (2003) 9(16) Part 2 Supp. pp. 61 05S-61 06S.
Shabbeer, S. et al., "Focus on deacetylation for therapeutic benefit," I Drugs 2005 United Kingdom (2005) (2):144-154.
Wingo, P.A. et al., "Cancer Statistics," CA Cancer Journal for Clinicians (1995) 45:8-30.
International Search Report (ISR) and Written Opinion (WO) of the International Search Authority for PCT/GB2006/000391.
Budillon, A et aL., "Multiple-target drugs: inhibitors of heat shock protein 90 and of histone deacetylase," Curr Drug Targets (2005) 6:337-351.
Byers, T., "What can randomized controlled trials tell us about nutrition and cancer prevention?" CA Cancer Clin_ (1999) 49:353-361.
Finn, P.W. et aL., "Novel sulfonamide derivatives as inhibitors of histone deacetylase," Helvetica Chimica Acta (2005) 88:1630-1657.
Granziero, L et al., "Adoptive immunotherapy prevents prostate cancer in a transgenic animal mode," Eur. J. ImmunoL (1999) 29:1127-1138.
Moradei, O. et aL., "Histone deacetylase inhibitors: latest developments, trends and prospects," Curr. Med. Chern.—Anti-Cancer Agents (2005) 5:529-560.
Rose et al. Second-line therapy with paclitaxel and carboplatin for recurrent disease following first-line therapy with paclitaxel and platinum in ovarian or peritoneal carcinoma. JCO. Apr. 1998, vol. 16, No. 4. 1494-1497.
Moore, P.S. et aL., "Gene expression profiling after treatment with the histone deacetylase inhibitor trichostatin A reveals altered expression of both pro- and anti-apoptotic genes in pancreatic adenocarcinoma cells," Biochim. Biophys. Acta., Sep. 17, 2004, vol. 1693, No. 3, pp. 167-176.
Stapnes, C. et aL., "Functional characteristics and gene expression profiles of primary acute myeloid leukaemia cells identify patient subgroups that differ in susceptibility to histone deacetylase inhibitors," Int J. OneaL, Dec. 2007, vol. 31, No. 6, pp. 1529-1538.
Yamagishi, S. et aL., "Expression of dihydropyrimidine dehydrogenase, thymidylate synthase, p53 and p21 in metastatic liver tumor from colorectal cancer after 5-fluorouracil-based chemotherapy," Anti-cancer Res., Mar.-Apr. 2005, vol. 25, No. 28, pp. 1237-1242.

(56) References Cited

OTHER PUBLICATIONS

Lee, J.H. et aL, "Histone deacetylase inhibitor enhances 5-fluorouracil cytotoxicity by down-regulating thymidylate synthase in human cancer cells," MoL Cancer Ther., Dec. 2006, vol. 5, No. 12, pp. 3085-3095.

Gimsing, P. et aL, A phase I clinical trial of the histone deacetylase inhibitor belinostat in patients with advanced hematological neoplasia. Eur J HaematoL Sep. 2008, vol. 81, No. 3, pp. 170-176.

Steele, N. L. et aL, A phase 1 pharmacokinetic and pharmacodynamic study of the histone deacetylase inhibitor belinostat in patients with advanced solid tumors. Clin. Cancer Res. Feb. 1, 2008, vol. 14, No. 3, pp. 804-810.

Advani, R. et aL, 2007, "Belinostat (PXD1 01) in patients with recurrent or refractory peripheral or cutaneous T-cell lymphoma: results of a phase II study," American Society for Hematology, vol. 110, Abstract No. 3453.

Avis, K.E. et aL (editors), 1992, "Pharmaceutical Dosage Forms: parenteral medications," second edition, pp. 514-518.

Gimseng et aL, 2005, "Activity of the histone deacetylase (HDAC) inhibitor PXD1 01 in preclinical studies and in a phase I study in patients with advanced hematological tumors," American Society of Hematology, vol. 106, Abstract No. 3337.

Gimseng, P. et aL, 2009, "Belinostat: a new broad acting antineoplastic histone deacetylase inhibitor," Expert Opin. Investig, Drugs, vol. 18, pp. 501-508.

MacKay, H. J. et al., 2007, "A phase II trial of the histone de acetylase inhibitor belinostat (PXD1 01) in patients with platinum resistant epithelial ovarian tumors and micropapillary/borderline (LMP) ovarian tumors. A trial of the PMH phase II consortium," AACR-NCI-EORTC Annual Meeting 2007, American Association for Cancer Research: Molecula Targets and Cancer Therapeutics.

Sinha et al., 2007, "A phase I/II study of the safety and anticancer activity of IV-administered belinostat (PXD1 01) plus carboplatin (C) or paclitaxel (P}, or both in patients with advanced solid tumours," 2007 Annual Meeting of the American Society of Clinical Oncology, Abstract No. 3574.

Sullivan, D. et al., 2006, "A Phase II Study of PXD1 01 in Advanced Multiple Myeloma," 2006, Annual Meeting of the American Society for Hematology, 2006, ASH Annual Meeting Abstracts, Part 1, vol. 108, Abstract 3583.

Hirano, A et al. "Application of Arginine to Increase the Solubility of Poorly Water-Soluble Compounds." J. of 1 Proteomics & Bioinformatics, Proceedings of the Joint 2nd Pacific Rim International conference on Protein Science and 4th Asian-Oceania Human Proteome Organization, Cairns, Australia, Jun. 22-26, 2008; Abstract No. 220.

Hoshikawa, Y. et al. "Trichostatin A Induces Morphological Changes and Gelsolin Expression by Inhibiting Histone Deacetylase in Human Carcinoma Cell Lines." Exp. Cell. Res., 1994; 214(1): 189-197.

Hockly, E. et al. "Suberoylanilide Hydroxamic Acid, a Histone Deacetylase Inhibitor, Ameliorates Motor Deficits in a Mouse Model of Huntington's Disease." Proc. Natl. Acad. Sci. USA, 2003; 100(4): 2041-2046.

Howe, L. et al. "Histone Acetyltransferase Complexes and Their Link to Transcription." Crit. Rev. Eukaryot. Gene Expr., 1999; 9(3-4): 231-243.

Iavarone et al. "E2F and Histone Deacetylase Mediate Transforming Growth Factor & Repression of cdc25A During Keratinocyte Cell Cycle Arrest." Mol. Cell Biol., 1999; 19(1 ):916-922.

Kao et al. "Isolation of a Novel Histone Deacetylase Reveals that Class I and Class II Deacetylases Promote SMRT-mediated Repression." Genes & Dev., 2000; 14(1 ): 55-66.

Kasim, N.A. et al. "Molecular Properties of WHO Essential Drugs and Provisional Biopharmaceutical Classification." Mol. Pharma, Sep. 2003; 1(1): 85-96.

Kim, Y.B. et al. "Oxamflatin is a Novel Antitumor Compound that Inhibits Mammalian Histone Deacetylase." Oncogene, 1999; 18(15): 2461-2470.

Kimura et al. "Dual Modes of Action of Platelet-Derived Growth Factor and its Inhibition by Trichostatin-A for DNA Synthesis in Primary Cultured Smooth Muscle Cells of Rat Aorta." Bioi. Pharm. Bull., 1994; 17(3):399-402.

Kitamura, K. et al. "Histone Deacetylase Inhibitor But Not Arsenic Trioxide Differentiates Acute Promyelocytic Leukemia Cells with t(11 ;17) in Combination with All-Trans Retinoic Acid." Br. J. Haematol., 2000; 108(4):696-702.

Kouzarides, T. "Histone Acetylases and Deacetylases in Cell Proliferation." Curr. Opin. Genet. Dev., 1999; 9(1 ):40-48.

Kuusisto et al. "Ubiquitin-Binding Protein p62 Expression is Induced during Apoptosis and Proteasomal Inhibition in Neuronal Cells." Biochem. Biophys. Res. Commun., 2001; 280(1 ): 223-228.

Laherty, C. D. et al. "Histone Deacetylases Associated with the mSin3 Corepressor Mediate Mad Transcriptional Repression." Cell, May 1997; 89(3): 349-356.

Lin, R.J. et al. "Role of the Histone Deacetylase Complex in Acute Promyelocytic Leukaemia." Nature, Feb. 1998; 391(6669): 811-814.

McCaffrey et al. "Induction of y-Giobin by Histone Deacetylase Inhibitors." Blood, Sep. 1997; 90(5):2075-2083.

Mielnicki et al. "Epigenetic Regulation of Gelsolin Expression in Human breast Cancer Cells." Exp. Cell. Res., 1999; 249(1):161-176.

Mura, P. et al. "Ternary systems of faproxen with hydroxypropyl-beta-cyclodextrin and aminoacids." Inti. J. Pharm., 2003; 260(2): 293-302.

Murata, T. et al., "Solubility of monoalkyl phosphate in water in the presence of arginine and triton, and solubilization of methyl yellow through the mixed micelle," Phosphorus Research Bulletin, (2008), vol. 22, pp. 41-47.

Ng, H.H. et al. "Histone Deacetylases: Silencers for Hire." Trends Biochem. Sci., 2000; 25(3):121-126.

Niki et al. "A Histone Deacetylase Inhibitor, Trichostatin A, Suppresses Myofibroblastic Differentiation of Rat Hepatic Stellate Cells in Primary Culture." Hepatol., 1999; 29(3):858-867.

Onishi et al. "Antibacterial Agents that Inhibit Lipid A Biosynthesis." Science, Nov. 1996; 274(5289): 939-940.

Pazin, M.J. et al. "What's Up and down with Histone Deacetylation and Transcription?" Cell, 1997; 89(3):325-328.

Saunders, N. et al. "Histone Deacetylase Inhibitors as Potential Anti-Skin Cancer Agents." Cancer Res., 1999; 59(2):399-404.

Spencer, VA et al. "Role of Covalent Modifications of Histones in Regulating Gene Expression." Gene, 1999; 240(1):1-12.

Strickley, R. "Solubilising Excipients in Oral and Injectable Formulations." Pharm. Res., 2004; 21 (2): 201-230.

Takahashi, I. et al. "Selective Inhibition of IL-2 Gene Expression by Trichostatin A, a Potent Inhibitor of Mammalian Histone Deacetylase." J. Antibiot. (Tokyo), 1996; 49(5):453-457.

Taunton, J. et al. "A Mammalian Histone Deacetylase Related to the Yeast Transcriptional Regulator Rpd3p." Science, 1996; 272(5260): 408-411.

Tsuji et al. "A New Antifungal Antibiotic, Trichostatin." J. Antibiot. (Tokyo), 1976; 29(1 ): 1-6.

Ueda, H. et al. "FR901228, a Novel Antitumor Bicyclic Depsipeptide Produced by Chromobacterium Violaceum No. 968." J. Antibiot. (Tokyo), 1994; 47(3):315-323.

Van Den Wyngaert et al., "Cloning and characterization of human histone deacetylase 8," FEBS L., 2000, Vo. 478, No. 1-2, pp. 77-83.

Vigushin et al. "Trichostatin A is a Histone Deacetylase Inhibitor with Potent Antitumor Activity against Breast Cancer in vivo." Clin. Cancer Res., 2001; 7(4):971-976.

Wolff, et al.: Burger's Medicinal Chemistry and Drug Discovery—Fifth Ed. New York: John Wiley & Sons, 1996; vol. 1, pp. 975-977.

Wong, J. et al. "Distinct Requirements for Chromatin Assembly in Transcriptional Repression by Thyroid Hormone Receptor and Histone Deacetylase." EMBO J., 1998; 17(2):520-534.

Yang, W.M. et al. Transcriptional Repression of YY1 is Mediated by Interaction with a Mammalian Homolog of the Yeast Global Regulator RPD3. Proc. Natl. Acad. Sci. USA, 1996; 93(23): 12845-12850.

(56) References Cited

OTHER PUBLICATIONS

Yang, W.M. et al. "Isolation and Characterization of cDNAs Corresponding to an Additional Member of the Human Histone Deacetylase Gene Family." J. Bioi. Chem., 1997; 272(44): 28001-28007.

* cited by examiner

PXD101/ALIMTA ON A549
(24H ALIMTA; 48H COTREATMENT)

PXD101/ALIMTA ON NCI-H460
(24H ALIMTA; 48H COTREATMENT)

COMBINATION THERAPIES USING HDAC INHIBITORS

RELATED APPLICATIONS

This application is a continuation of U.S. application Ser. No. 11/815,372 filed Aug. 2, 2007, which is a national phase application of PCT International Application No. PCT/GB06/00391 filed Feb. 3, 2006, which is related to: U.S. provisional patent application 60/649,991 filed 3 Feb. 2005; and U.S. provisional patent application 60/735,662 filed 10 Nov. 2005; the contents of all of which are incorporated herein by reference in their entirety.

FIELD OF THE INVENTION

The present invention relates to methods for treating cancer. More specifically, the present invention relates to methods for treating cancer, such as lung cancer, multiple myeloma, lymphoma, and epithelial ovarian cancer, in a subject, said methods comprising administering to a patient in need thereof a therapeutically effective amount of a histone deacetylase inhibitor (e.g., PXD-101 or its analogs), and a second amount or dose of a (i.e., another) chemotherapeutic agent (e.g., dexamethasone or 5-fluorouracil) and/or an epidermal growth factor receptor (EGFR) inhibitor (e.g., Tarceva®).

BACKGROUND OF THE INVENTION

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

As used herein, "a," "an" and "the" include singular and plural referents unless the context clearly dictates otherwise. Thus, for example, reference to "an active agent" or "a pharmacologically active agent" includes a single active agent as well a two or more different active agents in combination, reference to "a carrier" includes mixtures of two or more carriers as well as a single carrier, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Multiple Myeloma

Multiple myeloma is a disseminated malignancy of plasma cells that affects approximately 14,600 new patients each year in the United States. The etiology of this rare blood disease, affecting mainly the middle-aged to elderly population, is largely unknown although genetic predisposition and environmental factors have been implicated. From onset, malignant plasma cells arising from clonal expansion accumulate in the bone marrow, producing abnormally high levels of immunoglobulins. Multiple myeloma is difficult to diagnose early because there may be no symptoms in early stage. Bone pain especially secondary to compression fractures of the ribs or vertebrae is the most common symptom.

Dexamethasone is a commonly used regimen for first-line treatment of this disease. More recently, combinations of vincristine, doxorubicin, and dexamethasone (VAD) have been used to treat multiple myeloma. However, these are not effective long-term treatments. Dexamethasone treatment has a response rate of approximately 25-35%.

In many patients, high-dose chemotherapy supported by autologous stem cell transplantation (ASCT) may prolong event-free survival if the procedure is performed within 12 months of initial diagnosis. However almost all patients receiving high-dose chemotherapy and an autologous peripheral stem cell transplant will ultimately relapse.

Lymphoma

Despite years of research into the development of new methods of treatment, cancers of the lymphatic system, or lymphomas, remain quite common. For example, more than 60,000 people in the United States are diagnosed with lymphoma each year, including more than 55,000 cases of non-Hodgkin's Lymphoma (NHL), and these numbers are constantly increasing. In addition, the prognosis for those affected by these diseases is often poor, as the survival rates for lymphoma patients remain low. Clearly, new methods for treating these diseases are needed.

While traditional treatments for lymphoma typically depend on the type of lymphoma as well as the medical history of the patient, first-line treatment for many lymphomas typically includes chemotherapy. Such chemotherapy will often entail the administration of a "cocktail" of compounds, e.g., the formulation CHOP, which includes cyclophosphamide, doxorubicin, vincristine, and prednisone. In addition, certain first-line cancer treatments also include other forms of cancer therapy, such as radiation therapy.

In many cases, patients respond initially to such first-line treatments, but subsequently suffer a relapse, i.e., a tumor reappears or resumes growing. Following one such relapse, patients are often treated with further chemotherapy, e.g., with CHOP or with other formulations, or, in some cases, the patients are treated with other procedures such as bone marrow transplantation. Again, in many cases, patients initially respond to such additional treatments, but subsequently suffer another relapse. In general, the more relapses a patient suffers, the less agreement there is in the art concerning optimal subsequent treatment. In other cases, a patient fails to respond at all to a treatment, even initially, and is thus said to have a refractory cancer. In such cases as well, little agreement exists in the art regarding optimal subsequent treatment.

Prostate Cancer

Prostate cancer is the most common cancer leading to death among United States men. Its incidence has increased considerably over the past two decades. This cancer is often initially responsive to hormone treatment, but then frequently progresses into a hormone-insensitive state that is not easily treated. Further, once the cancer spreads or metastasizes from the prostate gland to other tissues such as bone marrow, the cancer usually cannot be cured by presently available treatments, which are either too toxic or cannot reach the metastases. There is a dire need for new strategies to treat prostate cancers, including metastasized prostate cancers, with low toxicity.

Ovarian Cancer

Ovarian cancer is the fourth leading cause of cancer deaths among women in the United States and causes more deaths than all other gynecologic malignancies combined.

In the United States, a woman's lifetime risk of developing ovarian cancer is 1 in 70. In 1992, about 21,000 cases of ovarian cancer were reported, and about 13,000 women died from the disease. See, e.g., Chapter 321, Ovarian Cancer, Harrison's Principles of Internal Medicine, 13th ed., Isselbacher et al., eds., McGraw-Hill, New York (1994), pages 1853-1858; and American Cancer Society Statistics, Cancer J. Clinicians, 45:30 (1995). Epithelial ovarian cancer, the most common ovarian cancer, has a distinctive pattern of spread in which cancer cells migrate throughout the peritoneal cavity to produce multiple metastatic nodules in the visceral and parietal peritoneum and the hemidiaphragms. In addition, metastasis can occur to distant sites such as the liver, lung and brain. Early stage ovarian cancer is often asymptomatic and is detected coincidentally by palpating an ovarian mass on pelvic examination. In premenopausal patients, about 95% of these masses are benign. Even after menopause, 70% of masses are benign but detection of any enlargement requires evaluation to rule out malignancy. In postmenopausal women with a pelvic mass, a markedly elevated serum CA-125 level of greater than 65 U/mL indicates malignancy with a 96% positive predictive value. See, e.g., Chapter 321, Ovarian Cancer, Harrison's Principles of Internal Medicine, 13th ed., Isselbacher et al., eds., McGraw-Hill, New York (1994).

Epithelial ovarian cancer is seldom encountered in women less than 35 years of age. Its incidence increases sharply with advancing age and peaks at ages 75 to 80, with the median age being 60 years. The single most important risk factor for this cancer is a strong family history of breast or ovarian cancer. Oncogenes associated with ovarian cancers include the HER-2/neu (c-erbB-2) oncogene, which is overexpressed in a third of ovarian cancers, the fms oncogene, and abnormalities in the p53 gene, which are seen in about half of ovarian cancers. A number of environmental factors have also been associated with a higher risk of epithelial ovarian cancer, including a high fat diet and intake of lactose in subjects with relatively low tissue levels of galactose-1-phosphate uridyl transferase.

The internationally accepted first-line chemotherapy for advanced epithelial ovarian cancer is the combination of carboplatin and paclitaxel. Typical results are median progression-free survival (PFS) of 17-20 months and median survival of 3-5 years. Second-line treatment is determined by duration of remission. If relapse occurs within 6 months of the last treatment, patients are considered "platinum resistant." Re-treatment with a carboplatin/paclitaxel regimen in these patients is associated with a low response rate (15%) of short duration (3-6 months), and a median survival of approximately 12 months. For this patient population, there is a need for a more effective therapy.

Lung Cancer

Lung cancer is the leading cause of cancer mortality in the United States ("Cancer Facts and Figures 2003," American Cancer Society). Lung cancer is particularly insidious because symptoms of early-stage, localized disease are nonspecific and are frequently attributed to the effects of smoking. By the time the patient seeks medical attention, the disease is usually advanced so that complete surgical resection is possible in less than 30% of all cases, and the overall 5-year survival rate in less than 15%. See, e.g., "Cancer of the Lung: Cancer Screening and Early Detection," in Cancer Medicine, 5th Edition, Bast et al. eds., B.C. Decker Inc., Hamilton, Ontario, Canada.

Surgery and radiotherapy may be curative if a cancer is found early, but current drug therapies for metastatic disease are mostly palliative and seldom offer a long-term cure. Even with the new chemotherapies entering the market, improvement in patient survival is measured in months rather than in years, and the need continues for new drugs effective both in combination with existing agents as first line therapy and as second and third line therapies in treatment of resistant tumors.

HDAC Inhibitors

Histones are major protein components of chromatin. The regulation of chromatin structure is emerging as a central mechanism for the control of gene expression. As a general paradigm, acetylation of the c-amino groups of lysine residues in the amino-terminal tails of nucleosomal histones is associated with transcriptional activation, while deacetylation is associated condensation of chromatin and transcriptional repression. Acetylation and deacetylation of histones is controlled by the enzymatic activity of histone acetyltransferases (HATs) and histone deacetylases (HDACs). Several transcription factors including p53 and GATA-1 have also been shown to be substrates for HDACs.

Prototypical HDAC inhibitors, such as the natural products trichostatin A (TSA) and suberoyl hydroxamic acid (SAHA), induce the expression of genes associated with cell cycle arrest and tumor suppression. Phenotypic changes induced by HDAC inhibitors include G1, and G2/ M cell cycle arrest and apoptosis in tumor cells. Antitumor activity has been demonstrated in vivo in animal models with a number of HDAC inhibitors, including PXD-101.

PXD-101 is a potent HDAC inhibitor that belongs to the hydroxymate-type of histone deacetylase inhibitors, which for various members of the group has shown pronounced in vitro and in vivo (pre-clinical and early clinical trials) activity against myeloma and lymphoma.

SUMMARY OF THE INVENTION

The present invention is based upon the discovery that histone deacetylase (HDAC) inhibitors, such as PXD-101, can be used in combination with chemotherapeutic agents and/or epidermal growth factor receptor (EGFR) inhibitors to provide therapeutically effective anticancer effects. Furthermore, an unexpected synergistic interaction between the HDAC inhibitor and the chemotherapeutic agent or the EGFR inhibitor results, wherein the combined effect is greater than the additive effect resulting from administration of the two treatments each at a therapeutic dose.

Thus, one aspect of the present invention relates to a method for the treatment of cancer, wherein the method comprises administering to a patient in need thereof, a first amount or dose of a histone deacetylase (HDAC) inhibitor, such as PXD-101, and a second amount or dose of a (i.e., another) chemotherapeutic agent, such as dexamethasone or 5-fluorouracil, or an epidermal growth factor receptor (EGFR) inhibitor, such as Tarceva®. The first and second amounts or doses together comprise a therapeutically effective amount.

Another aspect of the present invention pertains to use of a histone deacetylase (HDAC) inhibitor, such as PXD101, in the manufacture of a medicament for the treatment of cancer, wherein said treatment comprises treatment with (i) said histone deacetylase inhibitor and (ii) another chemotherapeutic agent, such as dexamethasone or 5-fluorouracil, or an epidermal growth factor receptor (EGFR) inhibitor, such as Tarceva®.

Another aspect of the present invention pertains to use of another chemotherapeutic agent, such as dexamethasone or 5-fluorouracil, or an epidermal growth factor receptor (EGFR) inhibitor, such as Tarceva®, in the manufacture of a medicament for the treatment of cancer, wherein said treatment comprises treatment with (i) a histone deacetylase (HDAC) inhibitor, such as PXD-101, and (ii) said another chemotherapeutic agent or epidermal growth factor receptor (EGFR) inhibitor.

The treatment procedures described herein can take place sequentially in any order, simultaneously, or a combination thereof. For example, the first treatment procedure, administration of a histone deacetylase (HDAC) inhibitor, can take place prior to the second treatment procedure, administration of a (i.e., another) chemotherapeutic agent or a epidermal growth factor receptor (EGFR) inhibitor; after the second treatment procedure; at the same time as the second treatment procedure; or a combination thereof. For example, a total treatment period can be decided for the HDAC inhibitor. The second treatment can be administered prior to onset of treatment with the HDAC inhibitor, or following treatment with the HDAC inhibitor. In addition, second treatment treatment can be administered during the period of HDAC inhibitor administration, but does not need to occur over the entire HDAC inhibitor treatment period.

The combination therapy can provide a therapeutic advantage in view of the differential toxicity associated with the two treatment modalities. More specifically, treatment with HDAC inhibitors can lead to hematologic toxicity, whereas chemotherapy treatments can be toxic to tissue adjacent the tissue site. As such, this differential toxicity can permit each treatment to be administered at its therapeutic dose, without increasing patient morbidity. Surprisingly however, the therapeutic effects achieved as a result of the combination treatment are enhanced or synergistic, for example, significantly better than additive therapeutic effects.

DETAILED DESCRIPTION OF THE INVENTION

Figure 1:
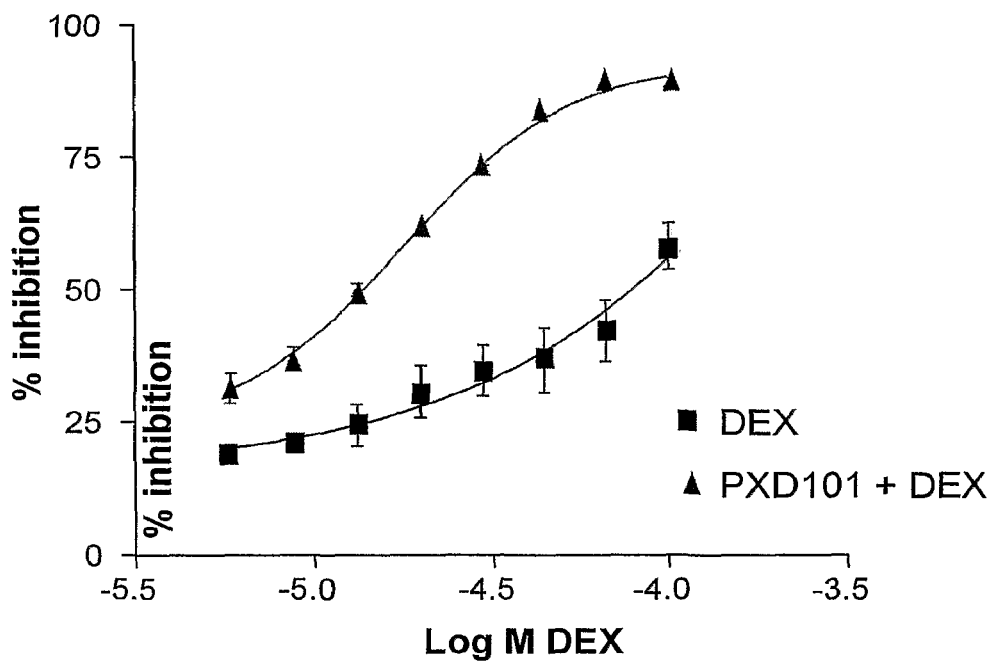
FIG. 1 depicts a graph (% inhibition vs. Log M DEX) demonstrating the results of a combination study involving PXD-101 and dexamethasone on a myleoma cell line (i.e., U266 cells): PXD-101 pre-incubation, followed by PXD-10130 dexamethasone). The lower curve is DEX only and the upper curve is PXD-101+DEX.

The present invention relates to methods for the treatment of cancer. The methods comprise administering to a patient in need thereof a first amount or dose of a histone deacetylase (HDAC) inhibitor, such as PXD-101, and a second amount or dose of a (i.e., another) chemotherapeutic agent, such as dexamethasone or 5-fluorouracil, or an epidermal growth factor receptor (EGFR) inhibitor, such as Tarceva®. The first and second amounts or doses together comprise a therapeutically effective amount.

(It is intended that histone deacetylase (HDAC) inhibitor is different from the chemotherapeutic agent or an EGFR inhibitor; that is, that the combination therapy is treatment with at least two different agents.)

In one embodiment, the second amount or dose is a second amount or dose of a (i.e., another) chemotherapeutic agent.

In one embodiment, the second amount or dose is a second amount or dose of an epidermal growth factor receptor (EGFR) inhibitor.

In one embodiment, the second amount or dose is a second amount or dose of a compound selected from: Cisplatin, 5-Fluorouracil, Oxaliplatin, Topotecan, Gemcitabine, Docetaxel, Doxorubicin, Tamoxifen, Dexamethasone, 5-Azacytidine, Chlorambucil, Fludarabine, Tarceva®, Alimta®, Melphalan, and pharmaceutically acceptable salts and solvates thereof.

In one embodiment, the method provides an anticancer effect which is synergistic.

As used herein, the terms "treatment of cancer" and "cancer treatment" refer to partially or totally inhibiting, delaying, or preventing the progression of cancer, including cancer metastasis; inhibiting, delaying, or preventing the recurrence of cancer, including cancer metastasis; or preventing the onset or development of cancer (chemoprevention) in a mammal, for example a human.

As used herein, the term "therapeutically effective amount" is intended to qualify the combined amount of the first and second treatments in the combination therapy. The combined amount will achieve the desired biological response. In the present invention, the desired biological response is treatment of cancer, i.e., partial or total inhibition, delay, or prevention of the progression of cancer, including cancer metastasis; inhibition, delay, or prevention of the recurrence of cancer, including cancer metastasis; or the prevention of the onset or development of cancer (chemoprevention) in a mammal, for example a human.

The combination therapy of the present invention is suitable for use in the treatment of a wide variety of cancers. As used herein, the term "cancer" refers to tumors, neoplasms, carcinomas, sarcomas, leukemias, lymphomas, and the like. For example, cancers include, but are not limited to, leukemias and lymphomas such as cutaneous T-cell lymphoma (CTCL), noncutaneous peripheral T-cell lymphoma, lymphomas associated with human T-cell lymphotropic virus (HTLV), for example, adult T-cell leukemia/lymphoma (ATLL), acute lymphocytic leukemia, acute nonlymphocytic leukemias, chronic lymphocytic leukemia, chronic myelogenous leukemia, Hodgkin's Disease, non-Hodgkin's lymphomas, and multiple myeloma, childhood solid tumors such as brain tumors, neuroblastoma, retinoblastoma, Wilms' Tumor, bone tumors, and soft-tissue sarcomas, common solid tumors of adults such as head and neck cancers (e.g., oral, laryngeal, and esophageal), genitourinary cancers (e.g., prostate, bladder, renal, uterine, ovarian, testicular, rectal, and colon), lung cancer, breast cancer, pancreatic cancer, melanoma and other skin cancers, stomach cancer, brain cancer, liver cancer and thyroid cancer.

In one embodiment, the cancer to be treated by the methods disclosed herein is lung cancer.

In one embodiment, the cancer to be treated by the methods disclosed herein is multiple myeloma.

In one embodiment, the cancer to be treated by the methods disclosed herein is lymphoma.

In one embodiment, the cancer to be treated by the methods disclosed herein is epithelial ovarian cancer.

Histone Deacetylases and Histone Deacetylase Inhibitors

Histone deacetylases (HDACs) are involved in the reversible acetylation of histone and non-histone proteins (p53, tubulin, and various transcription factors). Mammalian HDACs have been ordered into three classes based upon their similarity to known yeast factors. Class I HDACs (HDACs 1, 2, 3 and 8) bear similarity to the yeast RPD3 protein, are located in the nucleus and are found in complexes associated with transcriptional co-repressors. Class II HDACs (HDACs 4, 5, 6, 7 and 9) are similar to the yeast HDA1 protein, and have both nuclear and cytoplasmic subcellular localization. Class III HDACs form a structurally distant class of NAD dependent enzymes that are related to the yeast SIR2 proteins.

Compounds that have been shown to inhibit HDAC activity fall into five structurally diverse classes: (1) hydoxamic acids; (2) cyclic tetrapeptides; (3) aliphatic acids; (4) benzamides; and (5) electrophillic ketones.

Hydroxamic acids were among the first HDAC inhibitors identified and these agents helped define the model pharmacophore for HDAC inhibitors. The linker domain of these agents is comprised of linear or cyclic structures, either saturated or unsaturated, and the surface recognition domain is generally a hydrophobic group, most often aromatic. Phase I and II clinical trials are currently on-going for several hydoxamic acid-based HDAC inhibitors, including PXD-101.

PXD-101 is a highly potent HDAC inhibitor that blocks proliferation of diverse tumor cell lines at low micromolar potency ($IC_{50}$ 0.08-2.43 µM) and HDAC enzyme activity ($IC_{50}$ 9-110 nM). In xenograft models, PXD-101 slows tumor growth in a dose dependent manner and is particularly active in leukemic mouse models. In addition, PXD-101 causes cell cycle arrest and apoptosis in rapidly proliferating cells. Thus, hydoxamic acid-based HDAC inhibitors are suitable for use in the present invention.

In one embodiment, the histone deacetylase (HDAC) inhibitor is selected from compounds represented by the following formula:

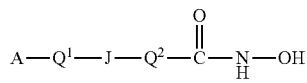

wherein:
A is an unsubstituted phenyl group;
$Q^1$ is a covalent bond, a $C_{1-7}$alkylene group, or a $C_{1-7}$alkenylene group;

J is:

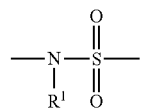

$R^1$ is hydrogen, $C_{1-7}$alkyl, $C_{3-20}$heterocyclyl, $C_{5-20}$aryl, or $C_{5-20}$aryl-$C_{1-7}$alkyl; and
$Q^2$ is:

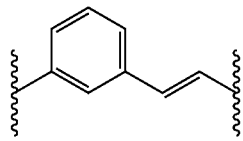 [SMILES: */C=C/c1cccc(*)c1]

and pharmaceutically acceptable salts and solvates thereof.

In one embodiment, $Q^1$ is a covalent bond or a $C_{1-7}$alkylene group.

In one embodiment, $Q^1$ is a covalent bond.

In one embodiment, $Q^1$ is a $C_{1-7}$alkylene group.

In one embodiment, $Q^1$ is —$CH_2$—, —$C(CH_3)$—, —$CH_2CH_2$—, —$CH_2CH(CH_3)$—, —$CH_2CH(CH_2CH_3)$—, —$CH_2CH_2CH_2$—, or —$CH_2CH_2CH_2CH_2$—.

In one embodiment, $Q^1$ is a $C_{1-7}$alkenylene group.

In one embodiment, $Q^1$ is —CH=CH— or —CH=CH—$CH_2$—.

In one embodiment, $R^1$ is hydrogen, $C_{1-7}$alkyl, $C_{3-20}$heterocyclyl, or $C_{5-20}$aryl.

In one embodiment, $R^1$ is hydrogen.

In one embodiment, $R^1$ is $C_{1-7}$alkyl.

In one embodiment, $R^1$ is -Me, -Et, -nPr, -iPr, -nBu, -iBu, -sBu, or -tBu.

In one embodiment, $R^1$ is -Me, -nBu, or -iBu

In one embodiment, $R^1$ is $C_{3-20}$heterocyclyl.

In one embodiment, $R^1$ is $C_{5-20}$aryl.

In one embodiment, $R^1$ is phenyl.

In one embodiment, $R^1$ is $C_{5-20}$aryl-$C_{1-7}$alkyl.

In one embodiment, $R^1$ is benzyl.

In one embodiment, the histone deacetylase (HDAC) inhibitor is selected from the following compounds, and pharmaceutically acceptable salts or solvates thereof

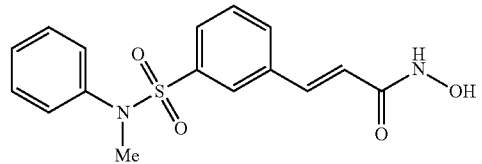

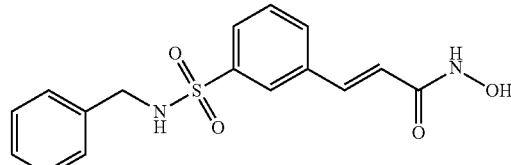

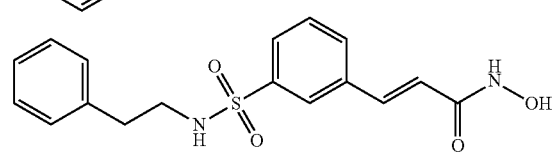

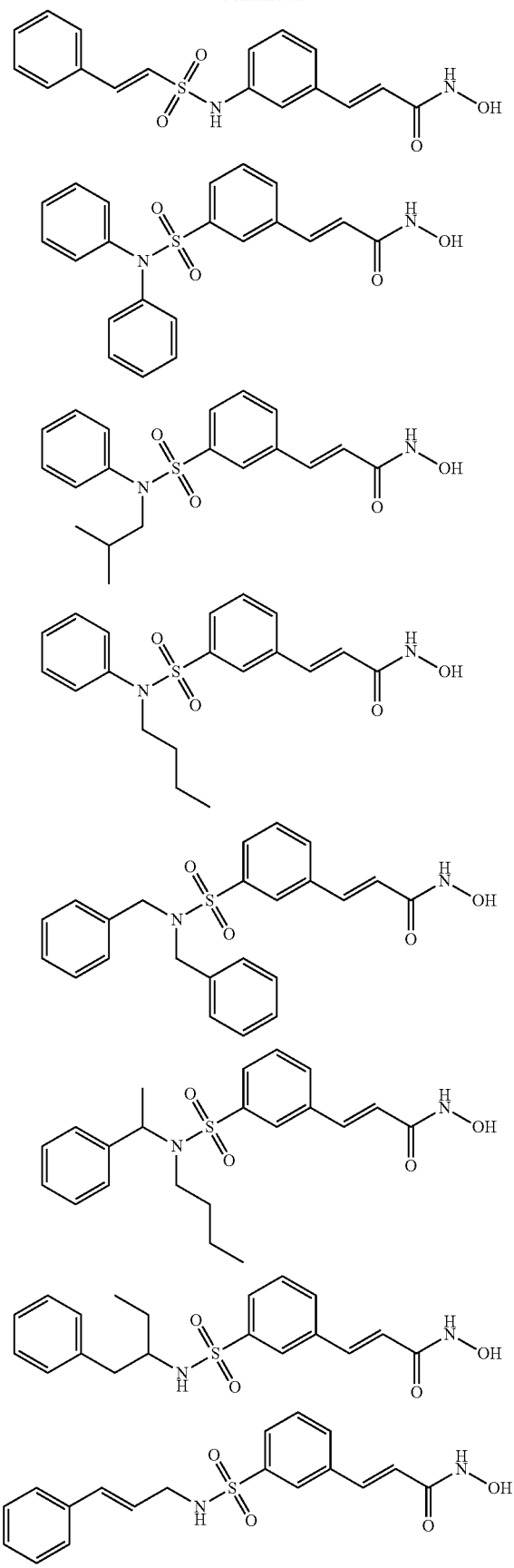

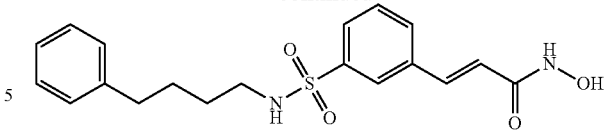

In one embodiment, the histone deacetylase (HDAC) inhibitor is selected from PXD-101, which is represented by the following formula, and pharmaceutically acceptable salts or solvates thereof:

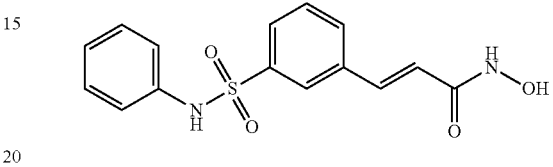

Other histone deacetylase (HDAC) inhibitors suitable for use in the present invention include the compounds disclosed in U.S. patent application Ser. Nos. 10/381,790; 10/381,794; and 10/381,791; the contents of each of which are hereby incorporated by reference in their entirety.

Stereoisomers

This invention is intended to encompass, in addition to the use of the above listed compounds, the use of stereoisomers of such compounds and mixtures thereof.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 (by mole) mixture of enantiomers is referred to as a racemic mixture. Many of the compounds described herein can have one or more chiral centers and therefore can exist in different enantiomeric forms. If desired, a chiral carbon atom can be designated with an asterisk (*). When bonds to the chiral carbon atom are depicted as straight lines in the formulas of the invention, it is understood that both the (R) and (S) configurations of the chiral carbon atom, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When the HDAC inhibitors described herein contain one chiral center, the compounds exist in two enantiomeric forms. The enantiomers can be resolved by methods known to those skilled in the art, for example by formation of diastereoisomer salts which can be separated, for example, by crystallization (See, e.g., CRC Handbook of Optical Resolutions via Diastereomeric Salt Formation by David Kozma (CRC Press, 2001)); formation of diastereoisomer derivatives or complexes which can be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers can be synthesized by asymmetric synthesis using optically active reagents, substrates, catalysts or solvents, or by converting one enantiomer into the other by asymmetric transformation. This invention is intended to encompass, in addition to the use of the above listed compounds, the use of each enantiomer and mixtures of enantiomers, such as the specific 50:50 (by mole) mixture referred to as a racemic mixture.

Designation of a specific absolute configuration at a chiral carbon of the compounds is understood to mean that the designated enantiomeric form of the compounds is in enantiomeric excess (ee) or in other words is substantially free from the other enantiomer. For example, the "R" forms of the compounds are substantially free from the "S" forms of the compounds and are; thus, in enantiomeric excess of the "S" forms. Conversely, "S" forms of the compounds are substantially free of "R" forms of the compounds and are, thus, in enantiomeric excess of the "R" forms. Enantiomeric excess, as used herein, is the presence of a particular enantiomer at greater than 50%. For example, the enantiomeric excess can be about 60% or more, such as about 70% or more, for example about 80% or more, such as about 90% or more. In a particular embodiment when a specific absolute configuration is designated, the enantiomeric excess of depicted compounds is at least about 90%. In a more particular embodiment, the enantiomeric excess of the compounds is at least about 95%, such as at least about 97.5%, for example, at least 99% enantiomeric excess.

When a compound has two or more chiral carbon atoms it can have more than two optical isomers and can exist in diastereoisomeric forms. For example, when there are two chiral carbon atoms, the compound can have up to 4 optical isomers and 2 pairs of enantiomers ((S,S)/(R,R) and (R,S)/(S,R)). The pairs of enantiomers (e.g., (S,S)/(R,R)) are mirror image stereoisomers of one another. The stereoisomers which are not mirror-images (e.g., (S,S) and (R,S)) are diastereomers. The diastereoisomer pairs can be separated by methods known to those skilled in the art, for example chromatography or crystallization and the individual enantiomers within each pair can be separated as described above. This invention is intended to encompass, in addition to the use of above listed compounds, the use of each diastereoisomer of such compounds and mixtures thereof.

Salts and Solvates

The active compounds disclosed herein can, as noted above, be prepared in the form of their pharmaceutically acceptable salts. Pharmaceutically acceptable salts are salts that retain the desired biological activity of the parent compound and do not impart undesired toxicological effects. Examples of pharmaceutically acceptable salts are discussed in Berge et al., 1977, "Pharmaceutically Acceptable Salts," J. Pharm. Sci., Vol. 66, pp. 1-19.

The active compounds disclosed can, as noted above, be prepared in the form of their solvates. The term "solvate" is used herein in the conventional sense to refer to a complex of solute (e.g., active compound, salt of active compound) and solvent. If the solvent is water, the solvate may be conveniently referred to as a hydrate, for example, a hemihydrate, monohydrate, dihydrate, trihydrate, tetrahydrate, and the like.

Prodrugs

This invention is intended to encompass, in addition to the use of the above listed compounds, the use of pro-drugs of the compound (e.g., HDAC inhibitors) disclosed herein. A prodrug of any of the compounds can be made using well known pharmacological techniques.

Homologs and Analogs

This invention is intended to encompass, in addition to the use of the above listed compounds, the use of homologs and analogs of such compounds. In this context, homologs are molecules having substantial structural similarities to the above-described compounds and analogs are molecules having substantial biological similarities regardless of structural similarities.

Chemotherapeutic Agents

The chemotherapeutic agents suitable for use in the present invention include one or more other anti-tumor substances, for example those selected from, for example, mitotic inhibitors, for example vinblastine; alkylating agents, for example cisplatin, carboplatin, and cyclophosphamide; inhibitors of microtubule assembly, like paclitaxel or other taxanes; antimetabolites, for example 5-fluorouracil, capecitabine, cytosine arabinoside, and hydroxyurea, or, for example, intercalating antibiotics, for example, adriamycin and bleomycin; immunostimulants, for example trastuzumab; DNA synthesis inhibitors, for example, gemcitabine; enzymes, for example asparaginase; topoisomerase inhibitors, for example etoposide; biological response modifiers, for example interferon; and anti-hormones, for example, antioestrogens such as tamoxifen or, for example, antiandrogens, such as (4'-cyano-3-(4-fluorophenylsulphonyl)-2-hydroxy-2-methyl-3'-(trifluoromethyl)-propionanilide, or other therapeutic agents and principles as described in, for example, DeVita, V. T., Jr., Hellmann, S., Rosenberg, S. A.; in: Cancer: Principles & Practice of Oncology, 5th ed., Lippincott-Raven Publishers (1997).

In one embodiment, the chemotherapeutic agent is dexamethasone.

In one embodiment, the chemotherapeutic agent is 5-fluorouracil.

EGFR Inhibitors

As used herein, the term "EGFR inhibitor" refers to a molecule having the ability to inhibit a biological function of a native epidermal growth factor receptor (EGFR). Accordingly, the term "inhibitor" is defined in the context of the biological role of EGFR. While preferred inhibitors herein specifically interact with (e.g., bind to) an EGFR, molecules that inhibit an EGFR biological activity by interacting with other members of the EGFR signal transduction pathway are also specifically included within this definition. A preferred EGFR biological activity inhibited by an EGFR inhibitor is associated with the development, growth, or spread of a tumor. EGFR inhibitors, without limitation, include peptides, non-peptide small molecules, antibodies, antibody fragments, antisense molecules, and oligonucleotide decoys.

In one embodiment, the EGFR inhibitor is Tarceva®.

Some Preferred Chemotherapeutic Agents and EGFR Inhibitors

Examples of some preferred chemotherapeutic agents and EGFR inhibitors include: Cisplatin, 5-Fluorouracil, Oxaliplatin, Topotecan, Gemcitabine, Docetaxel, Doxorubicin, Tamoxifen, Dexamethasone, 5-Azacytidine, Chlorambucil, Fludarabine, Tarceva®, Alimta®, Melphalan.

Thus, in one embodiment, the treatment comprises treatment with (i) a histone deacetylase (HDAC) inhibitor, such as PXD-101, and (ii) a compound selected from: Cisplatin, 5-Fluorouracil, Oxaliplatin, Topotecan, Gemcitabine, Docetaxel, Doxorubicin, Tamoxifen, Dexamethasone, 5-Azacytidine, Chlorambucil, Fludarabine, Tarceva®, Alimta®, Melphalan, and pharmaceutically acceptable salts and solvates thereof.

Modes and Doses of Administration

The methods of treatment of the present invention comprise administering to a patient in need thereof a first amount or dose of a histone deacetylase (HDAC) inhibitor, such as PXD-101, in a first treatment procedure, and a second amount or dose of a (i.e., another) chemotherapeutic agent, such as dexamethasone or 5-fluorouracil, or an epidermal growth factor receptor (EGFR) inhibitor, such as Tarceva®, in a second treatment procedure. The first and second amounts together comprise a therapeutically effective amount. In some embodiments, the combination therapy results in a synergistic effect.

The term "patient", as used herein, refers to the recipient of the treatment. Mammalian and non-mammalian patients are included. In one embodiment, the patient is a mammal. In one embodiment, the patient is a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), caprine (e.g., a goat), a primate, simian (e.g., a monkey or ape), a monkey (e.g., marmoset, baboon), an ape (e.g., gorilla, chimpanzee, orangutang, gibbon), or a human. In one embodiment, the patient is human, canine, feline, murine, bovine, ovine, porcine, or caprine.

In one embodiment, the patient is a human.

Administration of HDAC Inhibitor

The histone deacetylase (HDAC) inhibitors of the invention can be administered in oral forms such as tablets, capsules (each of which includes sustained release or timed release formulations), pills, powders, granules, elixers, tinctures, suspensions, syrups, and emulsions.

Likewise, the histone deacetylase (HDAC) inhibitors can be administered in intravenous (bolus or infusion), intraperitoneal, subcutaneous, or intramuscular form, all using forms well known to those of ordinary skill in the pharmaceutical arts.

The histone deacetylase (HDAC) inhibitors can be administered in the form of a depot injection or implant preparation which can be formulated in such a manner as to permit a sustained release of the active ingredient. The active ingredient can be compressed into pellets or small cylinders and implanted subcutaneously or intramuscularly as depot injections or implants. Implants can employ inert materials such as biodegradable polymers or synthetic silicones, for example, Silastic®, silicone rubber, or other polymers, e.g., manufactured by the Dow-Corning Corporation.

The HDAC inhibitor can also be administered in the form of liposome delivery systems, such as small unilamellar vesicles, large unilamellar vesicles and multilamellar vesicles. Liposomes can be formed from a variety of phospholipids, such as cholesterol, stearylamine, or phosphatidylcholines.

The HDAC inhibitors can also be delivered by the use of monoclonal antibodies as individual carriers to which the compound molecules are coupled.

The HDAC inhibitors can also be prepared with soluble polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the HDAC inhibitors can be prepared with biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates, and cross linked or amphipathic block copolymers of hydrogels.

Dosage Regimens

The dosage regimen utilizing the HDAC inhibitors can be selected in accordance with a variety of factors including type, species, age, weight, sex and the type of cancer being treated; the severity (i.e., stage) of the cancer to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease.

Dosage Rates and Formulations

Oral dosages of histone deacetylase (HDAC) inhibitors, when used to treat the desired cancer (e.g., in a human), can range between about 2 mg to about 2000 mg per day, such as from about 20 mg to about 2000 mg per day, such as from about 200 mg to about 2000 mg per day. For example, oral dosages can be about 2, about 20, about 200, about 400, about 800, about 1200, about 1600 or about 2000 mg per day. It is understood that the total amount per day can be administered in a single dose or can be administered in multiple dosing such as twice, three or four times per day.

For example, a patient can receive between about 2 mg/day to about 2000 mg/day, for example, from about 20 to 2000 mg/day, such as from about 200 to about 2000 mg/day, for example from about 400 mg/day to about 1200 mg/day. A suitably prepared medicament for once a day administration can thus contain between about 2 mg and about 2000 mg, such as from about 20 mg to about 2000 mg, such as from about 200 mg to about 1200 mg, such as from about 400 mg/day to about 1200 mg/day. The HDAC inhibitors can be administered in a single dose or in divided doses of two, three, or four times daily. For administration twice a day, a suitably prepared medicament would therefore contain half of the needed daily dose.

Intravenously or subcutaneously, the patient would receive the HDAC inhibitor in quantities sufficient to deliver between about 3 to 1500 $mg/m^2$ per day, for example, about 3, 30, 60, 90, 180, 300, 600, 900, 1200 or 1500 $mg/m^2$ per day. Such quantities can be administered in a number of suitable ways, e.g., large volumes of low concentrations of HDAC inhibitor during one extended period of time or several times a day. The quantities can be administered for one or more consecutive days, intermittent days, or a combination thereof per week (7 day period). Alternatively, low volumes of high concentrations of HDAC inhibitor during a short period of time, e.g., once a day for one or more days either consecutively, intermittently, or a combination thereof per week (7 day period). For example, a dose of 300 $mg/m^2$ per day can be administered for 5 consecutive days for a total of 1500 $mg/m^2$ per treatment. In another dosing regimen, the number of consecutive days can also be 5, with treatment lasting for 2 or 3 consecutive weeks for a total of 3000 $mg/m^2$ and 4500 $mg/m^2$ total treatment.

Typically, an intravenous formulation can be prepared which contains a concentration of HDAC inhibitor of between about 1.0 mg/mL to about 10 mg/mL, e.g. 2.0 mg/mL, 3.0 mg/mL, 4.0 mg/mL, 5.0 mg/mL, 6.0 mg/mL, 7.0 mg/mL, 8.0 mg/mL, 9.0 mg/mL and 10 mg/mL and administered in amounts to achieve the doses described above. In one example, a sufficient volume of intravenous formulation can be administered to a patient in a day such that the total dose for the day is between about 300 and about 1500 mg/m$^2$.

In a preferred embodiment, the histone deacetylase (HDAC) inhibitor is PXD-101 and is administered intravenously at a rate of 900 mg/m$^2$ every 24 hours.

Glucuronic acid, L-lactic acid, acetic acid, citric acid, or any pharmaceutically acceptable acid/conjugate base with reasonable buffering capacity in the pH range acceptable for intravenous administration of the HDAC inhibitor can be used as buffers. Sodium chloride solution wherein the pH has been adjusted to the desired range with either acid or base, for example, hydrochloric acid or sodium hydroxide, can also be employed. Typically, a pH range for the intravenous formulation can be in the range of from about 5 to about 12. A preferred pH range for intravenous formulation wherein the HDAC inhibitor has a hydroxamic acid moiety, can be about 9 to about 12. Consideration should be given to the solubility and chemical compatibility of the HDAC inhibitor in choosing an appropriate excipient.

Subcutaneous formulations, preferably prepared according to procedures well known in the art at a pH in the range between about 5 and about 12, also include suitable buffers and isotonicity agents. They can be formulated to deliver a daily dose of HDAC inhibitor in one or more daily subcutaneous administrations, e.g., one, two, or three times each day. The choice of appropriate buffer and pH of a formulation, depending on solubility of the HDAC inhibitor to be administered, is readily made by a person having ordinary skill in the art. Sodium chloride solution wherein the pH has been adjusted to the desired range with either acid or base, for example, hydrochloric acid, or sodium hydroxide, can also be employed in the subcutaneous formulation. Typically, a pH range for the subcutaneous formulation can be in the range of from about 5 to about 12. A preferred pH range for subcutaneous formulation wherein the HDAC inhibitor has a hydroxamic acid moiety, can be about 9 to about 12. Consideration should be given to the solubility and chemical compatibility of the HDAC inhibitor in choosing an appropriate excipient.

The HDAC inhibitors can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The HDAC inhibitors can be administered as active ingredients in admixture with suitable pharmaceutical diluents, excipients or carriers (collectively referred to herein as "carrier" materials) suitably selected with respect to the intended form of administration, that is, oral tablets, capsules, elixers, syrups, and the like, and consistent with conventional pharmaceutical practices.

For instance, for oral administration in the form of a tablet or capsule, the HDAC inhibitor can be combined with an oral, non-toxic, pharmaceutically acceptable, inert carrier such as lactose, starch, sucrose, glucose, methyl cellulose, microcrystalline cellulose, sodium croscarmellose, magnesium stearate, dicalcium phosphate, calcium sulfate, mannitol, sorbitol, and the like or a combination thereof. For oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn-sweeteners, natural and synthetic gums such as acacia, tragacanth, or sodium alginate, carboxymethylcellulose, microcrystalline cellulose, sodium croscarmellose, polyethylene glycol, waxes and the like. Lubricants that may be used in these dosage forms include sodium oleate, sodium stearate, magnesium stearate, sodium benzoate, sodium acetate, sodium chloride, and the like. Disintegrators include, without limitation, starch methyl cellulose, agar, bentonite, xanthan gum, and the like.

Suitable pharmaceutically acceptable salts of the histone deacetylase inhibitors described herein that are suitable for use in the method of the invention are conventional non-toxic salts and can include a salt with a base or an acid addition salt such as a salt with an inorganic base, for example, an alkali metal salt (e.g., lithium salt, sodium salt, potassium salt, etc.), an alkaline earth metal salt (e.g., calcium salt, magnesium salt, etc.), an ammonium salt; a salt with an organic base, for example, an organic amine salt (e.g., triethylamine salt, pyridine salt, picoline salt, ethanolamine salt, triethanolamine salt, dicyclohexylamine salt, N,N'-dibenzylethylenediamine salt, etc.) etc.; an inorganic acid addition salt (e.g., hydrochloride, hydrobromide, sulfate, phosphate, etc.); an organic carboxylic or sulfonic acid addition salt (e.g., formate, acetate, trifluoroacetate, maleate, tartrate, methanesulfonate, benzenesulfonate, p-toluenesulfonate, etc.); a salt with a basic or acidic amino acid (e.g., arginine, aspartic acid, glutamic acid, etc.); and the like.

Combination Therapy

The treatment procedures can take place sequentially in any order, simultaneously, or a combination thereof. For example, the first treatment procedure, administration of a HDAC inhibitor, can take place prior to (e.g., up to 7, 14, 21 days prior to) the second treatment procedure, administration of a chemotherapeutic agent or EGFR inhibitor, after (e.g., up to 7, 14, 21 days after) the second treatment procedure, at the same time as the second treatment procedure, or a combination thereof. In one embodiment, at least a part of the first treatment procedure is concurrent with a part of the second treatment procedure.

For example, a total treatment period can be decided for the HDAC inhibitor. The chemotherapeutic agent or EGFR inhibitor can be administered prior to onset of treatment with the HDAC inhibitor or following treatment with the HDAC inhibitor. In addition, the chemotherapeutic agent or EGFR inhibitor can be administered during the period of HDAC inhibitor administration but does not need to occur over the entire HDAC inhibitor treatment period.

In one embodiment, the present invention provides a method of treating cancer (e.g., multiple myeloma), wherein said method comprises administering to a patient, PXD-101 for several days prior to the administration of dexamethasone (DEX).

In one embodiment, the combination therapy is on a 21-day cycle wherein PXD-101 is administered every 24 hours for five days, then dexamethasone (DEX) and PXD-101 are administered on days 2-5 and 10-13.

In another embodiment, the present invention provides a method of treating cancer (e.g., epithelial ovarian cancer), wherein said method comprises administering to a patient, PXD-101 for several days prior to administering the carboplatin/paclitaxel regimen. In a specific embodiment, PXD-101 will be administered every 24 hours for 5 days every three weeks. In each cycle, the carboplatin/paclitaxel regimen will be administered on cycle day 3 after administration of PXD-101.

In another embodiment, the present invention provides a method of treating cancer (e.g., lymphoma), wherein said method comprises administering to a patient, PXD-101 in a first dose or amount and 5-FU in a second dose or amount, to provide therapeutically effective anti-cancer effects.

The histone deacetylase (HDAC) inhibitors and chemotherapeutic agents and EGFR inhibitors can also be used in a method of inhibiting cell proliferation in a cell comprising contacting the cell with a first amount of a compound capable of inhibiting a histone deacetylase (e.g., PXD-101) or a salt or solvate thereof, and contacting the cell with a second amount of a chemotherapeutic agent or EGFR inhibitor, to prevent, inhibit (fully or partially), or arrest cell proliferation. The cell can be a transgenic cell. In another embodiment the cell can be in a patient, such as a mammal, for example a human.

In one embodiment, the first amount to treat cancer in a cell is a contact concentration of HDAC inhibitor from about 1 pM to about 50 µM such as, from about 1 pM to about 5 µM, for example, from about 1 pM to about 500 nM, such as from about 1 pM to about 50 mM, for example, 1 pM to about 500 pM. In a particular embodiment, the concentration is less than about 5.0 µM. In another embodiment, the concentration is about 500 nM.

Kits

One aspect of the invention pertains to a kit or kit-of-parts comprising:

(a) a histone deacetylase (HDAC) inhibitor, such as PXD-101, preferably as a component of a pharmaceutically acceptable formulation, and preferably provided in a suitable container and/or with suitable packaging; and (b) another chemotherapeutic agent, such as dexamethasone or 5-fluorouracil, or an epidermal growth factor receptor (EGFR) inhibitor, such as Tarceva®, preferably as a component of a pharmaceutically acceptable formulation, and preferably provided in a suitable container and/or with suitable packaging;

wherein said kit or kit-of-parts is suitable for use in a method for treating cancer.

In one embodiment, the kit or kit-of-parts further comprises instructions, e.g., written instructions, for use, for example, instructions for administration, e.g., of the two drugs. In one embodiment, the instructions include a list of indications (e.g., cancer, types of cancer) for which combination of drugs is a suitable treatment.

In one embodiment, the kit or kit-of-parts further comprises appropriate reagents (e.g., buffers, solvents) and devices (e.g., tubes, syringes) for assembly and use (e.g., administration).

EXAMPLES

The following examples more fully illustrate the preferred embodiments of the invention. They should in no way be construed, however, as limiting the broad scope of the invention, as described herein.

Example 1

The effects of HDAC inhibitors in combination with standard chemotherapeutic agents were tested in vitro to determine the potential clinical use of an HDAC inhibitor (i.e., PXD-101), in combination chemotherapy. See, for example, the Data Annexes below.

WST-1 proliferation assays were used to assess the antiproliferative effects of drug combinations. For example, four myeloma cell lines (e.g., JJN3, LP-1, RPMI-8226, U266), the HCT116 human colon carcinoma cell line, and the ovarian cell line, A2780, and its platinum-resistant subline, A2780/cp7, among others, were used in the combination studies. A commercial program, CalcuSyn®, was employed to determine whether the combined effects are synergistic, antagonistic, or additive.

WST-1 Assay

Cells were cultured, exposed to PXD-101 alone or in combination with a chemotherapeutic agent, and incubated for a time, and the number of viable cells was then assessed using the Cell Proliferation Reagent WST-1 from Boehringer Mannheim (Cat. No. 1 644 807), described below.

Cells were plated in 96-well plates at 3-10×10$^3$ cells/well in 100 µL of culture medium. The following day, different concentrations of PXD-101 alone or in combination with a chemotherapeutic agent were added and the cells incubated at 37° C. for 48 hours. Subsequently, 10 µL/well of WST-1 reagent was added and the cells re-incubated for 1 hour. After the incubation time, absorbance was measured.

WST-1 is a tetrazolium salt which is cleaved to formazan dye by cellular enzymes. An expansion in the number of viable cells results in an increase in the overall activity of mitochondrial dehydrogenases in the sample. This augmentation in the enzyme activity leads to an increase in the amount of formazan dye formed, which directly correlates to the number of metabolically active cells in the culture. The formazan dye produced is quantified by a scanning multi-well spectrophotometer by measuring the absorbance of the dye solution at 450 nm wavelength (reference wavelength 690 nm).

Percent activity (% activity) in reducing the number of viable cells was calculated for each test compound as:

$$\% \text{ activity} = \{(S^c - B)/(S^o - B)\} \times 100$$

wherein $S^c$ denotes signal measured in the presence of the compound being tested, $S^o$ denotes signal measured in the absence of the compound being tested, and B denotes the background signal measured in blank wells containing medium only. The IC50 corresponds to the concentration which achieves 50% activity. IC50 values were calculated using the software package Prism® 3.0 (GraphPad Software Inc., San Diego, Calif., USA), setting top value at 100 and bottom value at 0.

Measurement of cell viability in the presence of increasing concentration of test compound at different time points is used to assess both cytotoxicity and the effect of the compound on cell proliferation.

The results were further analyzed using the Combination Index (CI) method with the CalcuSyn® program from Biosoft. A CI value of less than 1 indicates synergy; a CI value of 1 indicates an additive effect; and a CI value of greater than 1 indicates antagonism.

Using the CalcuSyn® program, the CI is determined by the isobologram equation CI=(D)1/(Dx)1+(D)2/(Dx)2. Drug 1 (D1) and drug 2 (D2) in combination inhibit X % and (Dx)1 and (Dx)2 are the doses of drug 1 and drug 2 alone that also inhibits X5. For each compound, the % growth values at each dose as determined in the WST-1 assay is used. CI values that are less than 1, equal to 1, or are greater than 1 indicate synergism, additive effect, or antagonism, respectively. CI's are compared at various percent inhibitory concentrations.

Results

PXD-101+5-FU

The anti-proliferative effects of combining PXD-101 and 5-FU were examined in a variety of cell lines (e.g., HT-116, A2780) and under varying conditions, e.g., simultaneously, 24 hours before, or 24 hours after administration of the chemotherapeutic agent 5-FU. The results of these experiments are summarized in FIG. 2 and Data Annex 3 which show the synergy of PXD-101 and 5-FU in the WST-1 anti-proliferative assay as calculated by CalcuSyn®.

Figure 2:
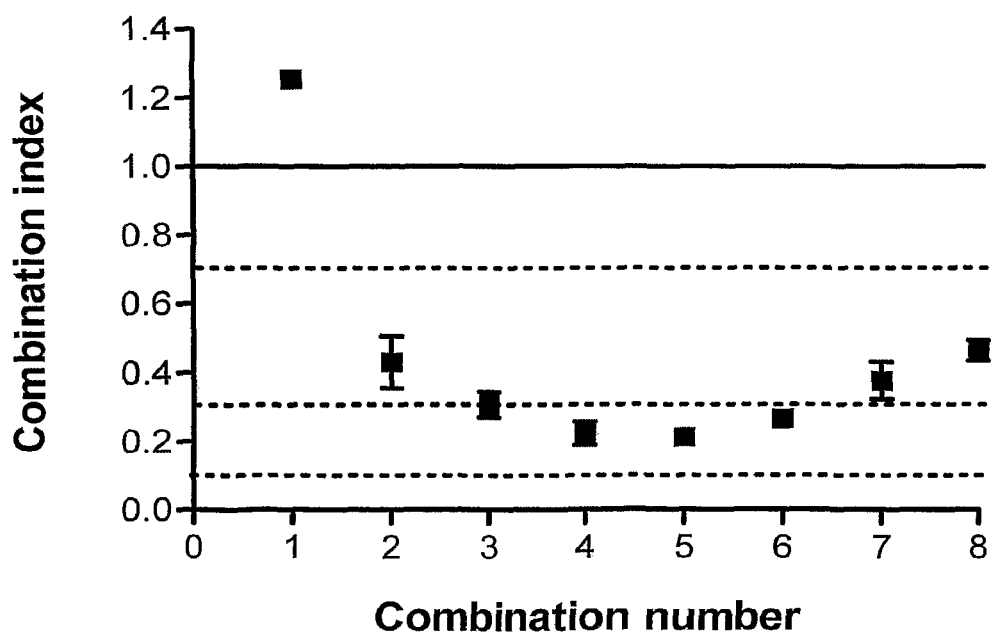
FIG. 2 depicts a graph (combination index vs. combination number) showing the synergy of PXD-101 and 5-FU in a WST-1 anti-proliferative assay as calculated by CalcuSyn® (HCT116, 24 hour PXD-101 +48 hour 5-FU ALONE, Combination). See also Data Annex 5.

FIG. 2 and Data Annex 5 depicts a graph and chart, respectively, showing the synergy of PXD-101 and 5-FU in a WST-1 anti-proliferative assay as calculated by CalcuSyn®.

To determine whether the combinations are additive, synergistic, or antagonistic, isobolograms are plotted and combination indices calculated using the commercial software program CalcuSyn®. In isobolograms, the X intercepts indicate the concentrations of one drug which results in a given percentage of growth inhibition and the Y intercepts indicate the concentrations at which the other drug inhibited cell growth. The data point that falls between the axes indicates the concentration of the drug combination that inhibits cell growth. The further above or below this data point deviates from the straight line joining the intercept, the more antagonistic or synergistic the effect, respectively. Combination data points that fall on or close to the line joining the intercepts indicates additive effects.

FIG. 1 depicts an isobologram for the combination of PXD-101 and 5-FU in a HCT116 cell line, wherein 5-FU was added alone 24 hours after PXD-101. The graph demonstrates that this combination produces a surprisingly synergistic effect.

In the lymphoma cell line, a synergistic effect was observed when 5-FU was added 24 hours after the administration of PXD-101.

Data Annex 8 shows that a synergy between PXD-101 and 5-FU exists also in vivo. In the Mouse P388 leukemia model, the survival of the mice treated with the drug combination is greater than the survival of those treated with each drug alone. Notably, there is also a synergy when mice are treated with PXD-101 and a combination of 5-FU and oxaliplatin (see Data Annex 9).

PXD-101 Fludarabine

There is a synergistic effect of PXD-101 and fludarabine in the mouse P388 model: the survival of the mice treated with the combination of drugs is greater than the survival of mice treated with each drug alone (see Data Annex 10).

PXD-101 and Other Chemotherapeutic Agents

L-phenylalanine mustard (PAM, melphalan) shows synergy with PXD-101 in a number of myeloma cell lines (see Data Annex 1). Furthermore, synergy can be seen between PXD-101 and other chemotherapeutic agents, specifically cisplatin, 5-FU, topotecan, gemcitabine, docetaxel, doxorubicin, tamoxifen, dexamethasaone, and 5-aazacytidine, in a number of tumour cell lines (see Data Annex 2). Finally, synergy of PXD-101 with chlorambucil, and synergy of PXD-101 with fludarabine, is seen in cell proliferation experiments in cultured lymphoma cells (see Data Annex 4).

PXD-101+Dexamethasone

The anti-proliferative effects of adding PXD-101 simultaneously (e.g., 48 hour co-incubations), 24 hr after, or 24 hr before adding the chemotherapeutic agent, dexamethasone to the JJN3, LP-1, RPMI-8226, U266 tumor cell lines were also examined by the methods described above.

When cells were treated with PXD-101 in combination with dexamethasone simultaneously (i.e., at 48 hour co-incubations), 24 hour PXD-101 then 48 hour PXD-101+DEX, or 24 hour DEX, then 48 hour PXD-101+DEX, synergistic effects were obtained for the LP-1, RPMI-8226, and U266 tumor cell lines over a range of concentrations (see Data Annex 1). Strong synergy (CI<0.3) was observed in the U266 cell line when PXD-101 was administered for 24 hours, followed by 48 hour PXD-101+DEX, and in the LP1 cell line when DEX was administered for 24 hours, followed by 48-hour co-incubation of PXD-101 and DEX over a range of concentrations and conditions (see Data Annex 1).

PXD-101+Doxorubicin

The myeloma cell lines (e.g., JJN3, LP-1, RPMI-8226, U266) were treated with PXD-101 and doxorubicin. As described above, the combined effects of these compounds on the myeloma cell lines was determined by plotting isobolograms and calculating combination indices.

Additive to synergistic effects were observed for this combination when PXD-101 and doxorubicin were co-incubated for 48 hours over a range of concentrations (see Data Annex 1 and Data Annex 2).

PXD-101+Vincristine

The myeloma cell lines (e.g., JJN3, LP-1, RPMI-8226, U266) were treated with PXD-101 and vincristine. As described above, the combined effects of these compounds on the myeloma cell lines was determined by plotting isobolograms and calculating combination indeces. Additive to synergistic effects were observed for this combination when PXD-101 and vincristine were co-incubated over a range of concentrations (see Data Annex 1).

PXD-101+Alimta®

Figure 6:
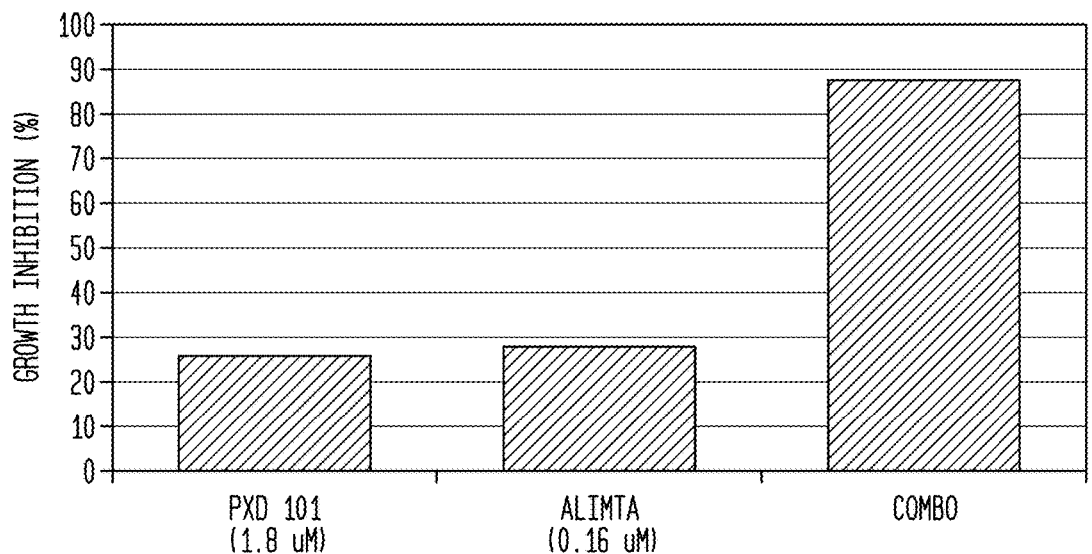
FIG. 6 depicts two bar graphs (in vitro growth inhibition (%)) for (top): PXD-101 (1.8 µM), Alimta® (0.16 µM), and the combination (PXD-101/Alimta® on A549, 24 hour Alimta®, 48 hour co-treatment); and (bottom): PXD-101 (1.8 µM), Alimta® (0.04 µM), and the combination (PXD-101/Alimta® on NCI-H460, 24 hour Alimta®, 48 hour co-treatment).
Figure 6:
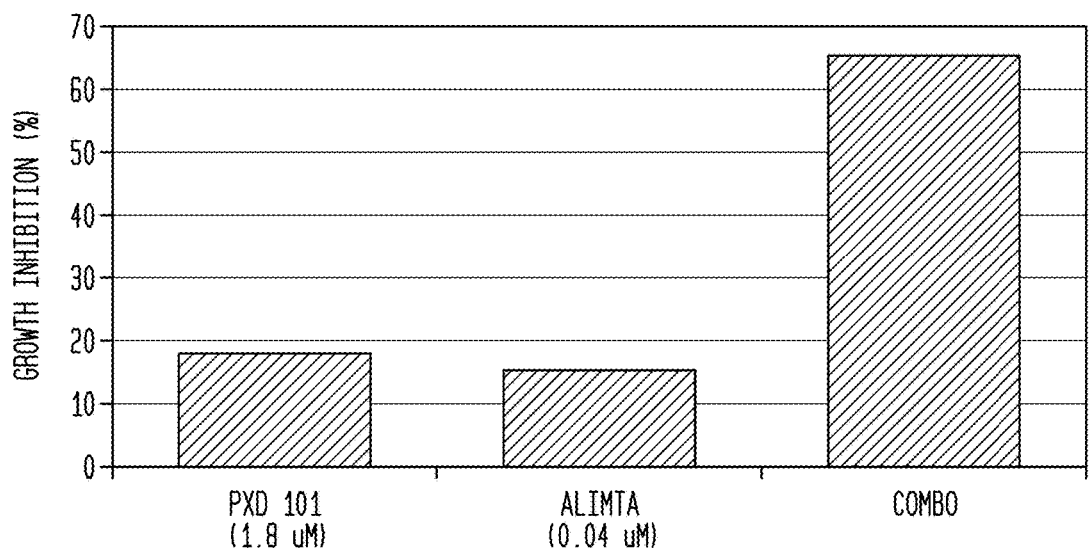

The antifolate pemetrexed (Alimta®) is marketed for use against lung cancers. There is a clear synergistic effect of combining PXD-101 with Alimta® in proliferation experiments using cultured cells (see Data Annex 12 and FIG. 6).

Discussion

This example reports the effect of combining PXD-101 with standard chemotherapeutics. There is strong synergy between PXD-101 and DEX when U266 cells are incubated with PXD-101 for 24 hours prior to the administration of DEX, and when LP1 cells are incubated with DEX for 24 hours prior to the administration of PXD-101 over a range of concentrations and conditions (See Data Annex 1 and FIG. 1).

Combination of PXD-101 with doxorubicin on myeloma cell lines produced additive to synergistic effects when the compounds were co-incubated over a range of concentrations and conditions (see Data Annex 1).

Similarly, combination of PXD-101 with cisplatin on ovarian cell lines produced additive to synergistic effects when the compounds were co-incubated over a range of concentrations and conditions (see Data Annex 2).

Moreover, combination of PXD-101 with 5-FU produced strong synergism in a variety of cell lines (e.g., ovarian cell lines, A2780 and OVCAR3, lung cell line, NYH, breast cancer cell line, MCF-7, and colon cancer cell lines, HT116 and HT116p53). In most circumstances, the strongest synergism was observed when 5-FU was added 24 hours after the administration of PXD-101. (See Data Annex 2.) In addition, the combination of PXD-101 and 5-FU produced synergistic effects in the lymphoma cell line when 5-FU was administered 24 hours after the administration of PXD-101.

Accordingly, the above combination studies identify effective therapeutic combinations for use in clinical trials of PXD-101.

Example 2

Clonogenic Assay

A clonogenic assay was performed essentially as described (Jensen et al., 1993) to determine the anti-proliferative effects of combinations involving PXD-101, in particular a combination involving PXD-101 and 5-FU.

Figure 3:
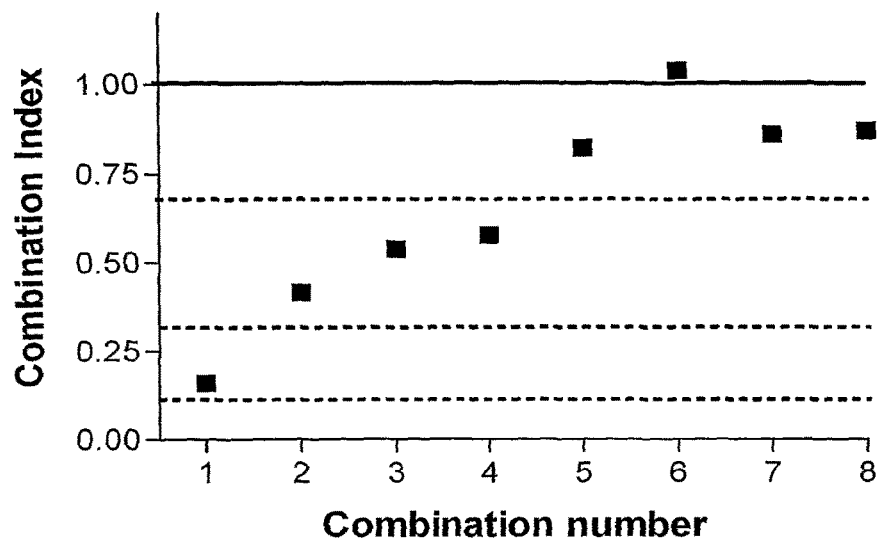
FIG. 3 depicts a graph (combination index vs. combination number) showing the synergy of PXD-101 and 5-FU in a clonogenic assay as calculated by CalcuSyn® (HCT116 PXD-101/5-FU 24 h co-incubation).

In this assay, HCT116 or p388 cells were exposed to combinations of PXD-101 and 5-FU for the indicated times. Cells were then plated in 0.3% agar in 6 cm petri dishes with sheep red blood cells as feeder layer in triplicate, and were incubated at 37° C. Plates were counted after 14-21 days. A summary of the results is provided in Data Annex 6. Data Annex 7 and FIG. 3 present the data underlying this summary, and shows the synergy of PXD-101 and 5-FU in the clonogenic assay as calculated by CalcuSyn®.

Data Annex 6 demonstrates that combinations of PXD-101 and 5-FU are synergistic to strongly synergistic in both cell lines when PXD-101 and 5-FU were co-incubated for 24 hours and when PXD-101 was administered 24 hours after the administration of 5-FU. The data also demonstrate that this combination produces strong synergistic effects when 5-FU is administered 24 hours after the administration of PXD-101.

Example 3

In vivo Studies

To investigate the tumour growth inhibitory effect of PXD-101 in a HCT116 colon cancer subcutaneous xenograft model (nu/nu mice), two PXD-101 doses were included, 60 and 100 mg/kg scheduled q1d ×5/week for 2 weeks. The chemo-sensitising effect of PXD-101 in combination with 5-FU was also investigated. The 5-FU dose was set at 15 mg/kg.

PXD101 caused significant tumour growth inhibition in a HCT-116 colon cancer xenograft model in nude mice. 5-FU was ineffective in the HCT116 model in the chosen dose regimen, which indicates suboptimal dosing.

Figure 4:
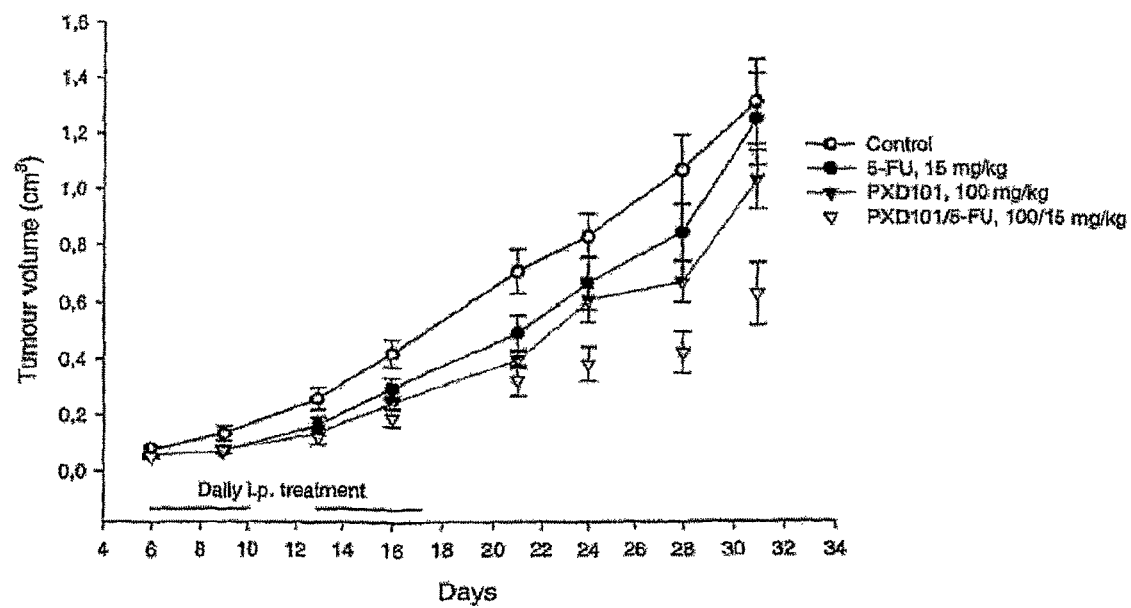
FIG. 4 depicts a graph (tumor volume (cm$^3$) vs. days) representing the chemo-sensitizing effect of PXD-101 (Control; 5-FU, 15 mg/kg; PXD-101, 100 mg/kg; PXD-101/5-FU, 100/15 mg/kg).

FIG. 4 shows the chemo-sensitising effect of PXD101. HCT116 colon cancer xenograph. Daily i.p. treatments with PXD101 (morning) and 5-FU (afternoon). Mean/SEM, n=10 (9).

Chemo-sensitising effect of PXD101 on 5-FU treatment was indicated. The results indicated synergistic effect of PXD101 and 5-FU after the first treatment cycle where single 5-FU therapy is ineffective at 15 mg/kg. FIG. 4 depicts a graph summarizing the chemo-sensitizing effects of PXD-101 in a HCT116 colon cancer xenograft.

P388 Mouse Model

P388 mouse leukemia cells were injected intrapertoneally (IP) into B6D1F1 female mice. PXD-101 and/or chemotherapeutic agent were administered IP on day 3, then daily for the required number of consecutive days. Kaplan-Meier survival distribution graphs are shown for each combination.

Example 4

Growth Inhibition Assays Involving EGFR Inhibitors and HDAC Inhibitors

The objective of this study was to determine whether PXD-101 monotherapy or combination therapy with Tarceva® effects the growth of A431 cells (human epidermoid carcinoma) or Calu-3 cells (human non-small cell lung cancer).

Materials and Methods:

Cells were plated at 3,000 cells/well in 96-well plates, treated with PXD-101 or Tarceva® (an EGFR-kinase inhibitor) alone or in combination at the indicated concentrations for 72 hours, and evaluated for growth/viability via the CellTiter-Glo assay described above.

Figure 5:
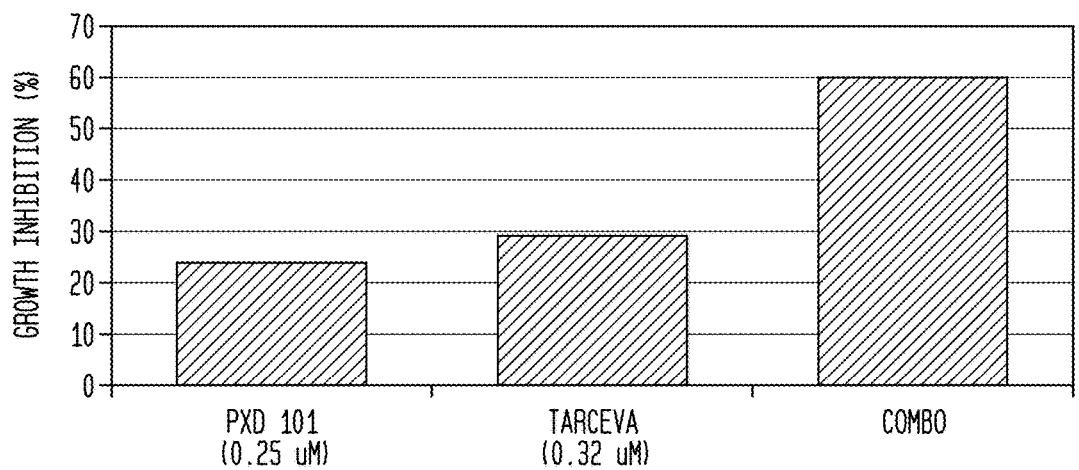
FIG. 5 depicts two bar graphs (in vitro growth inhibition (%)) for (top): PXD-101 (0.25 µM), Tarceva® (0.32 µM), and the combination (PXD-101/Tarceva® on Calu03, 72 hour co-treatment); and (bottom: PXD-101 (0.35 µM), Tarceva® (0.04 µM), and the combination (PXD-101/Tarceva® on HCC-4006, 72 hour co-treatment).
Figure 5:
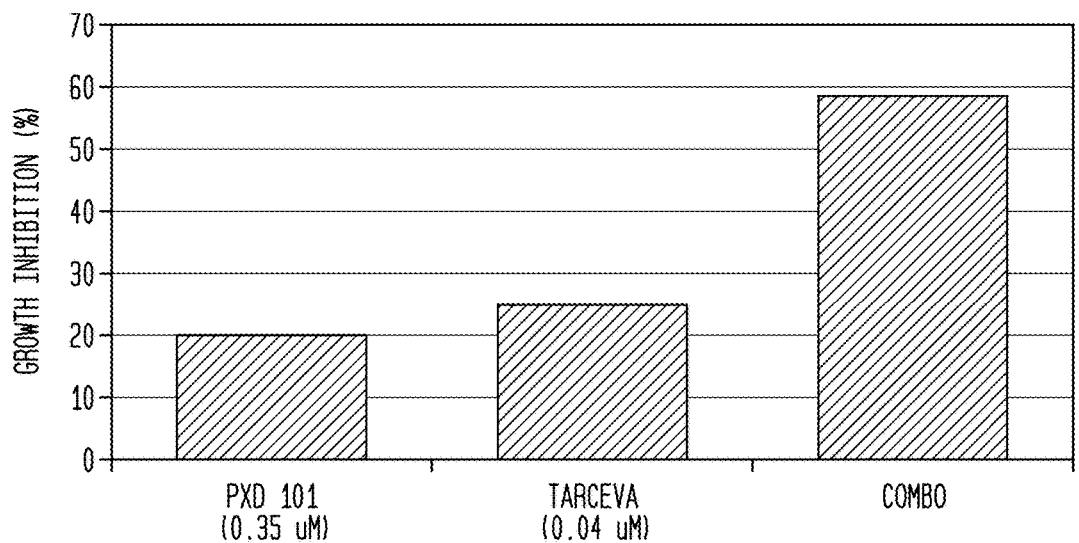

Results:

The combination of PXD-101+Tarceva® causes greater growth-inhibition than either drug used alone. See, for example, FIG. 5 and Data Annex 11. This effect is synergistic.

Conclusion:

PXD-101 used in combination with Tarceva® may be beneficial for the treatment of non-small cell lung cancer and perhaps other types of cancers.

Example 5

Western Blot

The objective of this study was to determine whether PXD-101 treatment effects EGFR protein levels.

Materials and Methods:

A431 cells (human epidermoid carcinoma) were plated at ~80% confluency in 6-well plates, treated with PXD-101 at the indicated concentrations for 24 hours, and then whole-cell lysates were harvested and analyzed by Western blotting using an anti-EGFR antibody. The blot was reprobed with an anti-actin antibody to control for lane loading.

Results:

PXD-101 treatment apparently decreases the level of EGFR protein in A431 cells.

Conclusion:

A431 cells are known to overexpress wild-type EGFR and to be sensitive to growth-inhibition by reagents that inhibit the EGFR pathway. The reduction of EGFR protein induced by PXD-101 may be one mechanism by which PXD-101 used alone is growth-inhibitory to these cells. Moreover, the PXD-101-mediated reduction in EGFR protein may provide a mechanistic rationale for the additive/synergistic growth-inhibition observed when PXD-101 is used in combination with Tarceva®.

ADDITIONAL DATA

Data Annex 1

Summary of MYELOMA combination studies with PXD101 in vitro. Numbers in brackets is a guide to the schedule used in each experiment (see below). Results in Table are those produced using "standard" combination protocol.

| | PXD101 Combined With: | | | |
|---|---|---|---|---|
| Cell Line | Vincristine | Doxorubicin | PAM | Dexa-methasone |
| JJN3 | −(1), +(2), ++(3) | +(1), −(2, 3) | +(1, 2), ++(3) | −(2) |
| LP-1 | −(2), +(1, 3) | ++(1), −(2, 3) | −(1, 3), +(2) | ++(1), ++(2), +++(3) |
| RPMI-8226 | ++(1), −(2, 3) | +(1, 2), ++(3) | +(1, 2), ++(3) | +(2) |

-continued

| Cell Line | PXD101 Combined With: | | | |
|---|---|---|---|---|
| | Vincristine | Doxorubicin | PAM | Dexa-methasone |
| U266 | +(1), −(2, 3) | ++(1), +(2), −(3) | +(1, 3) ++(2) | +++(2), ++(3) |

| At least three points fall on or below CI value corresponding to: | | |
|---|---|---|
| CI < 0.3 | very synergistic | +++ |
| CI 0.3-0.7 | synergistic | ++ |
| CI 0.7-1 | additive | + |
| CI > 1 | antagonistic | − |
| | not done | nd |

(1) 48 hour co-incubations
(2) 24 hour PXD101 then 48 hour PXD101 & compound
(3) 24 hour compound then 48 hour PXD101 & compound JJN3, RPMI 8226 & U266 cells are dexamethasone resistant.

Data Annex 2

Summary of the combination studies with PXD101 in vitro. Numbers in brackets is a guide to the schedule used in each experiment (see below).

| Cell Line | PXD101 Combined With: | | | |
|---|---|---|---|---|
| | Cisplatin | 5-FU | Topotecan | Gemcitabine |
| A2780 (ovarian) | ++(1, 3, 4, 7, 8, 12) | +++(3, 1) | ++(1) | ++(1) |
| A2780cp70 (ovarian) | ++(1), ++(4, 7, 8, 12) | nd | nd | nd |
| OVCAR3 (ovarian) | ++(1, 4, 8, 12), +++(7) | +++(1, 7), ++(11), +(3) | nd | nd |
| PC-3 (prostate) | ++(1, 4), +++(7, 8, 12) | ++(4) | +(1) | ++(1) |
| NYH (lung) | −(1, 4, 8, 12), +(7) | +++(4) | +(1) | ++(2) |
| MIA-PA-CA2 (pancreatic) | nd | nd | nd | −(6), −(4) |
| P-388 (leukaemic) | −(1), ++(4, 8) | −(7), +(1, 3, 8), ++(10) | −(1), ++(4) | +(1, 8) |
| MCF-7 (breast) | +(8), ++(1, 4, 7, 12) | ++(5), +++(4) | ++(1) | +(4, 6) |
| T47-D (breast) | nd | nd | nd | nd |
| MDA-MB-231 (breast) | nd | nd | nd | nd |
| HT-29 (colon) | +++(1, 7), ++(4, 8), +(12) | −(1), +(4), ++(3, 5, 8, 9), +++(7) | +(1) | ++(2) |
| HT116 (colon) | nd | ++(1, 11), +++(7) | nd | nd |
| HT116CMV (colon) | nd | ++(1, 7, 11) | nd | nd |
| HT116p53 (colon) | nd | ++(1, 11), +++(7) | nd | nd |
| LNCaP (prostate) | nd | nd | nd | nd |

Data Annex 2 (continued)

| Cell Line | PXD101 Combined With: | | | |
|---|---|---|---|---|
| | Docetaxel | Doxorubicin | Tamoxifen | Dexa-methasone |
| A2780 (ovarian) | nd | nd | nd | nd |
| A2780cp70 (ovarian) | nd | nd | nd | nd |
| OVCAR3 (ovarian) | −(1, 7, 8), +(4, 12) | nd | nd | nd |
| PC-3 (prostate) | +(1), ++(3) | −(1) | nd | −(1, 2, 14), +(13) |
| NYH (lung) | nd | nd | nd | nd |
| MIA-PA-CA2 (pancreatic) | nd | nd | nd | nd |
| P-388 (leukaemic) | nd | +(1), +(8) | nd | nd |
| MCF-7 (breast) | nd | −(1, 7) | −(1, 3, 11) +(12) | nd |
| T47-D (breast) | nd | +(1, 7) | +(1, 3, 11, 12) | nd |
| MDA-MB-231 (breast) | nd | +++(1) | −(3), +(11), ++(1) | nd |
| HT-29 (colon) | ++(1) | nd | nd | nd |
| HT116 (colon) | nd | nd | nd | nd |
| HT116CMV (colon) | nd | nd | nd | nd |
| HT116p53 (colon) | nd | nd | nd | nd |
| LNCaP (prostate) | nd | nd | nd | −(3) |

Data Annex 2 (Continued)

| Cell Line | PXD101 Combined With: | | | |
|---|---|---|---|---|
| | 5-Azacytidine | Alimta ® | Irinotecan | Oxaliplatin |
| A2780 (ovarian) | nd | nd | nd | nd |
| A2780cp70 (ovarian) | nd | nd | nd | nd |
| OVCAR3 (ovarian) | nd | nd | nd | nd |
| PC-3 (prostate) | nd | nd | nd | nd |
| NYH (lung) | nd | nd | nd | nd |
| MIA-PA-CA2 (pancreatic) | nd | nd | nd | nd |
| P-388 (leukaemic) | nd | nd | nd | nd |
| MCF-7 (breast) | ++(1, 4, 8) | nd | nd | nd |
| T47-D (breast) | +(7), ++(1, 4), +++(8), | nd | nd | nd |
| MDA-MB-231 (breast) | ++(1, 4, 7) +(8, 11), −(15) | nd | nd | nd |
| HT-29 (colon) | nd | nd | nd | nd |
| HT116 (colon) | nd | −(7), +(1, 2, 3, 4) ++(12) | −(1, 3), +(2), ++(4, 7, 12) | −(1) +(2, 3, 4, 7, 12) |
| HT116CMV (colon) | nd | nd | nd | nd |
| HT116p53 (colon) | nd | nd | nd | nd |

| Cell Line | PXD101 Combined With: | | | |
|---|---|---|---|---|
| | 5-Azacytidine | Alimta ® | Irinotecan | Oxaliplatin |
| LNCaP (prostate) | nd | nd | nd | nd |

| At least three points fall on or below CI value corresponding to: | | |
|---|---|---|
| CI < 0.3 | very synergistic | +++ |
| CI 0.3-0.7 | synergistic | ++ |
| CI 0.7-1 | additive | + |
| CI > 1 | antagonistic | – |
| | not done | nd |

| | |
|---|---|
| (1) | 48 hour co-incubations |
| (2) | 72 hour co-incubations |
| (3) | 24 hour PXD101 then 24 hour PXD101 & compound |
| (4) | 24 hour compound then 48 hour PXD101 & compound |
| (5) | 48 hour compound then 48 hour PXD101 & compound |
| (6) | 96 hour co-incubations |
| (7) | 24 hour PXD101 then 48 hour compound alone |
| (8) | 24 hour PXD101 then 48 hour PXD101 & compound |
| (9) | 24 hour PXD101 then 72 hour compound alone |
| (10) | 24 hour compound then 24 hour PXD101 & compound |
| (11) | 24 hour PXD101 then 24 hour compound alone |
| (12) | 24 hour compound then 48 hour PXD101 alone |
| (13) | 96 hour co-incubations |
| (14) | 48 hour PXD101 then 72 hour compound alone |
| (15) | 6 hour PXD101 then 24 hour compound |

Data Annex 3

| PXD-101 + 5-FU | |
|---|---|
| Cell Line | Combined Effect |
| A2780 (ovarian) | +++(3, 1) |
| OVCAR3 (ovarian) | +++(1, 7), +(11), +(3) |
| PC-3 (prostate) | ++(4) |
| NYH (lung) | +++(4) |
| P-388 (leukaemic) | –(7), +(1, 3, 8), ++(10) |
| MCF-7 (breast) | ++(5), +++(4) |
| HT-29 (colon) | –(1), +(4), ++(3, 5, 8, 9), +++(7) |
| HT116 (colon) | ++(1, 11), +++(7) |
| HT116CMV (colon) | ++(1, 7, 11) |
| HT116p53 (colon) | ++(1, 11), +++(7) |

| At least three points fall on or below CI value corresponding to: | | |
|---|---|---|
| CI < 0.3 | very synergistic | +++ |
| CI 0.3-0.7 | synergistic | ++ |
| CI 0.7-1 | additive | + |
| CI > 1 | antagonistic | – |

| | |
|---|---|
| (1) | 48 hour co-incubations |
| (2) | 72 hour co-incubations |
| (3) | 24 hour PXD101 then 24 hour. PXD101 & 5-FU |
| (4) | 24 hour compound then 48 hour PXD101 & 5-FU |
| (5) | 48 hour compound then 48 hour PXD101 & 5-FU |
| (6) | 96 hour co-incubations |
| (7) | 24 hour PXD101 then 48 hour FU-5 alone |
| (8) | 24 hour PXD101 then 48 hour PXD101 & FU-5 |
| (9) | 24 hour PXD101 then 72 hour FU-5 alone |
| (10) | 24 hour compound then 24 hour PXD101 & FU-5 |
| (11) | 24 hour PXD101 then 24 hour FU-5 alone |

Data Annex 4

Summary of LYMPHOMA combination studies with PXD101 in vitro. Numbers in brackets are a guide to the schedule used in each experiment (see below). Results in Table are those produced using "standard" combination protocol.

| | PXD combined with: | |
|---|---|---|
| Cell Line | Chlorambucil | Fludarabine |
| SU-DHL-4 | –(1, 3), ++(2) | –(2), +(1), ++(3) |

| At least three points fall on or below CI value corresponding to: | | |
|---|---|---|
| CI < 0.3 | very synergistic | +++ |
| CI 0.3-0.7 | synergistic | ++ |
| CI 0.7-1 | additive | + |
| CI > 1 | antagonistic | – |
| | not done | nd |

| | |
|---|---|
| (1) | 48 hour co-incubations |
| (2) | 24 hour PXD101 then 48 hour PXD101 & compound |
| (3) | 24 hour compound then 48 hour PXD101 & compound |

Data Annex 5

| WST-1 Assay | | | |
|---|---|---|---|
| Combination No. | PXD-101 (μM) | 5-FU (μM) | Combination Index |
| 1 | 0.187 | 2.22 | 1.253 |
| 2 | 0.28 | 3.33 | 0.429 |
| 3 | 0.42 | 5 | 0.307 |
| 4 | 0.63 | 7.5 | 0.222 |
| 5 | 0.945 | 11.25 | 0.212 |
| 6 | 1.42 | 16.88 | 0.265 |
| 7 | 2.13 | 25.31 | 0.375 |
| 8 | 3.195 | 37.97 | 0.462 |

Data Annex 6

Summary of Clonogenic Assay combination studies with PXD101/5-FU in vitro.

| Cell Line | 24 h co-incubations | 24 h PXD101 + 24 h 5-FU | 24 h 5-FU + 24 h PXD101 |
|---|---|---|---|
| P-388 | ++ | + | ++ |
| HCT-116 | ++ | +++ | +++ |

| At least three points fall on or below CI value corresponding to: | | |
| --- | --- | --- |
| CI < 0.3 | very synergistic | +++ |
| CI 0.3-0.7 | synergistic | ++ |
| CI 0.7-1 | additive | + |
| CI > 1 | antagonistic | − |
| | not done | nd |

Data Annex 7

| Clonogenic Assay | | | |
| --- | --- | --- | --- |
| Combination No. | PXD-101 (µM) | 5-FU (µM) | Combination Index |
| 1 | 100 | 135 | 0.16 |
| 2 | 50 | 90 | 0.416 |
| 3 | 25 | 60 | 0.538 |
| 4 | 12.5 | 40 | 0.577 |
| 5 | 6.25 | 26.67 | 0.823 |
| 6 | 3.125 | 17.78 | 1.04 |
| 7 | 1.5626 | 11.85 | 0.86 |
| 8 | 0.78125 | 7.9 | 0.871 |

Data Annex 8

In vivo synergy of 5-FU and PXD101 in the P388 mouse model.

| | | Cumulative Survival | | | | |
| --- | --- | --- | --- | --- | --- | --- |
| Time (days) | 5-FU (30) | 5-FU (30) + PXD101 (100) | 5-FU (30) + PXD101 (60) | PXD101 (100) | PXD101 (60) | Vehicle control |
| 9 | 1 | 1 | 1 | 1 | 1 | 0.70 |
| 10 | 1 | 1 | 1 | 1 | 1 | 0.43 |
| 11 | 1 | 1 | 1 | 0.85 | 1 | 0.15 |
| 12 | 1 | 1 | 1 | 0.43 | 0.70 | 0 |
| 13 | 1 | 1 | 1 | 0.43 | 0.15 | — |
| 14 | 1 | 1 | 1 | 0.15 | 0 | — |
| 15 | 0.85 | 1 | 1 | 0 | — | — |
| 16 | 0.55 | 1 | 1 | — | — | — |
| 17 | 0.15 | 1 | 1 | — | — | — |
| 18 | 0 | 1 | 0.85 | — | — | — |
| 19 | — | 1 | 0.30 | — | — | — |
| 20 | — | 0.43 | 0.15 | — | — | — |
| 21 | — | 0.30 | 0.15 | — | — | — |
| 22 | — | 0.15 | 0.15 | — | — | — |
| 23 | — | 0 | 0.15 | — | — | — |
| 24 | — | — | 0 | — | — | — |

Data Annex 9

In vivo synergy of PXD 101 with the combination of oxaliplatin and 5-FU in the P388 mouse model.

| | | | Cumulative Survival | | | |
| --- | --- | --- | --- | --- | --- | --- |
| Time (days) | 5-FU (50) | Oxali (5) | Oxali (5) + 5-FU (50) | PXD101 (100) + Oxali (5) + 5-FU (50) | PXD101 (60) + Oxali (5) + 5-FU(50) | Vehicle control |
| 9 | 1.00 | 0.45 | 1.00 | 1.00 | 1.00 | 0.85 |
| 10 | 0.55 | 0 | 0.55 | 1.00 | 1.00 | 0.75 |
| 11 | 0.15 | — | 0.30 | 1.00 | 1.00 | 0.45 |
| 12 | 0.15 | — | 0.30 | 1.00 | 0.85 | 0.35 |
| 13 | 0.15 | — | 0.30 | 1.00 | 0.85 | 0.35 |
| 14 | 0.15 | — | 0.30 | 1.00 | 0.85 | 0.35 |
| 15 | 0.15 | — | 0.30 | 1.00 | 0.85 | 0.20 |
| 16 | 0.15 | — | 0.30 | 0.85 | 0.85 | 0.15 |
| 17 | 0.15 | — | 0.30 | 0.70 | 0.70 | 0.15 |
| 18 | 0.15 | — | 0.30 | 0.55 | 0.45 | 0.10 |
| 19 | 0.15 | — | 0.30 | 0.55 | 0.30 | 0.10 |
| 20 | 0.15 | — | 0.30 | 0.55 | 0.30 | 0.10 |
| 21 | 0.15 | — | 0.30 | 0.55 | 0.30 | 0.10 |
| 22 | 0.15 | — | 0.30 | 0.45 | 0.30 | 0 |
| 23 | 0.15 | — | 0.30 | 0.45 | 0.30 | — |
| 24 | 0 | — | 0.30 | 0.45 | 0.15 | — |
| 25 | — | — | 0.30 | 0.45 | 0.15 | — |
| 26 | — | — | 0.30 | 0.30 | 0.15 | — |
| 27 | — | — | 0.30 | 0.30 | 0.15 | — |
| 28 | — | — | 0.15 | 0.15 | 0.15 | — |
| 29 | — | — | 0.15 | 0.15 | 0.15 | — |
| 30 | — | — | 0.15 | 0.15 | 0.15 | — |
| 31 | — | — | 0 | 0 | 0 | — |

Data Annex 10

In vivo synergy of PXD 101 with fludarabine in the P388 mouse model.

| | Cumulative Survival | | | |
| --- | --- | --- | --- | --- |
| Time (days) | Fludarabin (50) | PXD101 (100) + Fludarabin (50) | PXD101 (60) + Fludarabin (50) | Vehicle control |
| 8 | 1.00 | 1.00 | 1.00 | 0.70 |
| 9 | 0.85 | 1.00 | 1.00 | 0.55 |
| 10 | 0.55 | 1.00 | 1.00 | 0.40 |
| 11 | 0.40 | 1.00 | 1.00 | 0.30 |
| 12 | 0.40 | 1.00 | 1.00 | 0.30 |
| 13 | 0.40 | 1.00 | 1.00 | 0.30 |
| 14 | 0.40 | 0.50 | 1.00 | 0.30 |
| 15 | 0.30 | 0.35 | 0.55 | 0.30 |
| 16 | 0.30 | 0.17 | 0.55 | 0.15 |
| 17 | 0.15 | 0 | 0.30 | 0 |
| 18 | 0.15 | — | 0.30 | — |
| 19 | 0 | — | 0.15 | — |
| 20 | — | — | 0 | — |

Data Annex 11

Data from proliferation experiments using cultured cells, demonstrating the synergy of PXD101 with Tarceva®.

| Calu-3 (wtEGFR; moderately responsive to Tarceva ®) | | |
| --- | --- | --- |
| PXD101 (µM) | Tarceva ® (µM) | Combination Index |
| 0.0313 | 0.01 | 0.556 |
| 0.0625 | 0.0316 | 0.371 |
| 0.125 | 0.1 | 0.479 |
| 0.25 | 0.316 | 0.525 |
| 0.5 | 1.0 | 0.549 |
| 1.0 | 3.16 | 0.641 |

| HCC-4006 (mutant EGFR; strongly responsive to Tarceva ®) | | |
|---|---|---|
| PXD101 (μM) | Tarceva ® (μM) | Combination Index |
| 0.351 | 0.0391 | 0.447 |
| 0.527 | 0.078 | 0.294 |
| 0.79 | 0.156 | 0.154 |
| 1.185 | 0.313 | 0.166 |
| 1.778 | 0.625 | 0.245 |
| 2.667 | 1.25 | 0.309 |

| Range of CI | Description | Symbol |
|---|---|---|
| <0.1 | Very strong synergism | +++++ |
| 0.1-0.3 | Strong synergism | ++++ |
| 0.3-0.7 | Synergism | +++ |
| 0.7-0.85 | Moderate synergism | ++ |
| 0.85-0.90 | Slight synergism | + |
| 0.9-1.10 | Nearly additive | ± |
| 1.10-1.20 | Slight antagonism | − |
| 1.20-1.45 | Moderate antagonism | − − |

Data Annex 12

Data from proliferation experiments using cultured cells, demonstrating the synergy of PXD101 with Alimta®.

| A549 | | |
|---|---|---|
| PDX101 (μM) | Alimta (μM) | Combination Index |
| 0.351 | 0.0195 | 1.339 |
| 0.527 | 0.0293 | 0.694 |
| 0.79 | 0.0439 | 0.301 |
| 1.185 | 0.0658 | 0.179 |
| 1.778 | 0.0988 | 0.178 |
| 2.667 | 0.1482 | 0.231 |
| 4.0 | 0.2222 | 0.302 |
| 6.0 | 0.3333 | 0.338 |
| 9.0 | 0.5 | 0.557 |

| NCI-H460 | | |
|---|---|---|
| PDX101 (μM) | Alimta (μM) | Combination Index |
| 0.351 | 0.0196 | 0.893 |
| 0.527 | 0.0391 | 0.374 |
| 0.79 | 0.078 | 0.193 |
| 1.185 | 0.156 | 0.157 |
| 1.778 | 0.313 | 0.161 |
| 2.667 | 0.625 | 0.216 |
| 4.0 | 1.25 | 0.289 |
| 6.0 | 2.5 | 0.362 |
| 9.0 | 5.0 | 0.528 |

| Range of CI | Description | Symbol |
|---|---|---|
| <0.1 | Very strong synergism | +++++ |
| 0.1-0.3 | Strong synergism | ++++ |
| 0.3-0.7 | Synergism | +++ |
| 0.7-0.85 | Moderate synergism | ++ |
| 0.85-0.90 | Slight synergism | + |
| 0.9-1.10 | Nearly additive | ± |
| 1.10-1.20 | Slight antagonism | − |
| 1.20-1.45 | Moderate antagonism | − − |

Data Annex 13

In the following table, the median survival time for mice treated with PXD101 and 5-FU, alone or in combination, is listed together with minimum and maximum observed survival time within each group.

The percentage Increased Life Span (ILS%) was calculated as the median survival (treatment group) minus median survival (vehicle control) divided by median survival (vehicle control) multiplied with 100:

$$ILS\% = \frac{\text{Median survival (treatment group)} - \text{Median survival (vehicle control)}}{\text{Median survival (vehicle control)}} \times 100$$

The effect of PXD101 and 5-FU combined treatment was compared to 5-FU treatment alone using Log Rank statistic analysis and p-values<0.05 are considered statistical significant.

| | Survival time | | | | | |
|---|---|---|---|---|---|---|
| Treatment | Median survival | Min | Max | N | ILS % | P-value* |
| Untreated control | 10 | 9 | 11 | 10 | | |
| Vehicle control | 10 | 9 | 12 | 11 | | |
| 5-FU(30) | 16 | 15 | 18 | 12 | 60.0% | |
| PXD101(60) | 13 | 12 | 14 | 7 | 30.0% | |
| PXD101(100) | 12 | 11 | 14 | 7 | 20.0% | |
| PXD101(30) + 5-FU(30) | 19 | 17 | 19 | 5 | 90.0% | 0.022 |
| PXD101(60) + 5-FU(30) | 19 | 18 | 24 | 12 | 90.0% | <0.0001 |
| PXD101(100) + 5-FU(30) | 21 | 10 | 24 | 13 | 110.0% | <0.0001 |

P388 i.p. mouse leukemia tumour. Intraperitoneal treatment with PXD101 (mg/kg/treat) and 5-FU (mg/kg/treat) i.p. daily for 5 days starting day 3 after tumour implantation. ILS % percentage Increased Life Spand.
*Log Rank statistic: Compared to 5-FU (30 mg/kg) alone.

When P388 IP implanted mice were treated with PXD101 and 5-FU (MTD) in combination significantly prolonged survival was observed compared to when PXD101 or 5-FU was given as single treatment. A dose response effect of the PXD101 when added to the 5-FU treatment was indicated.

EQUIVALENTS

Those skilled in the art will recognize, or be able to ascertain using no more than routine experimentation, many equivalents to the specific embodiments of the invention described herein. Such equivalents are intended to be encompassed by the following claims.

Thus, while the preferred embodiments of the invention have been illustrated and described, it is to be understood that this invention is capable of variation and modification, and should not be limited to the precise terms set forth. The inventors desire to avail themselves of such changes and alterations which may be made for adapting the invention to various usages and conditions. Such alterations and changes may include, for example, different pharmaceutical compositions for the administration of the agents according to the present invention to a mammal; different amounts of agent in the compositions to be administered; different times and means of administering the agents according to the present invention; and different materials contained in the administration dose including, for example, combinations of different agents, or combinations of the agents according to the present invention together with other biologically active compounds for the same, similar or differing purposes than the desired utility of those agents specifically disclosed herein. Such changes and alterations also are intended to include modifications of the specific desired agents described herein in which such changes alter the agent in a manner as not to change the desired potential of the agent, but as to change solubility of the agent in the pharmaceutical composition to be administered or in the body, absorption of the agent by the body, protection of the agent for either shelf life or within the body until such time as the biological action of the agent is able to bring about the desired effect, and such similar modifications. Accordingly, such changes and alterations are properly intended to be within the full range of equivalents, and therefore within the purview of the following claims.

The invention and the manner and process of making and using it have been thus described in such full, clear, concise and exact terms so as to enable any person skilled in the art to which it pertains, or with which it is most nearly connected, to make and use the same.

The invention claimed is:

1. A method for treating non-small cell lung cancer comprising administering to a patient in need thereof,
    a first amount of a histone deacetylase (HDAC) inhibitor, and
    a second amount of an epidermal growth factor receptor (EGFR) inhibitor,
    wherein the first and second amounts together comprise a therapeutically effective amount,
    wherein the therapeutically effective amount has a synergistic effect compared to an effect of the first amount alone and an effect of the second amount alone,
    wherein the epidermal growth factor receptor (EGFR) inhibitor is selected from the group consisting of TARCEVA® and pharmaceutically acceptable salts and solvates thereof, and
    wherein the HDAC inhibitor is selected from the following compound and pharmaceutically acceptable salts and solvates thereof:

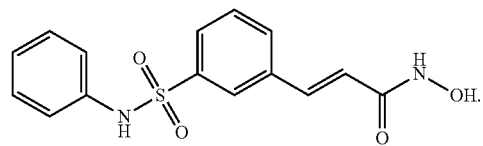 [SMILES: O=C(/C=C/c1cccc(S(=O)(=O)Nc2ccccc2)c1)NO]

* * * * *